(12) United States Patent
Speight et al.

(10) Patent No.: US 11,540,994 B2
(45) Date of Patent: Jan. 3, 2023

(54) REMOVAL OF BIOLOGICAL DEPOSITS

(71) Applicants: Meat & Livestock Australia Ltd, North Sydney (AU); Queensland University of Technology, Brisbane (AU)

(72) Inventors: Robert Speight, Brisbane (AU); Laura Navone, Brisbane (AU)

(*) Notice: Subject to any disclaimer, the term of this patent is extended or adjusted under 35 U.S.C. 154(b) by 262 days.

(21) Appl. No.: 16/753,126

(22) PCT Filed: Jun. 25, 2018

(86) PCT No.: PCT/AU2018/050639
§ 371 (c)(1),
(2) Date: Apr. 2, 2020

(87) PCT Pub. No.: WO2019/068133
PCT Pub. Date: Apr. 11, 2019

(65) Prior Publication Data
US 2020/0315943 A1    Oct. 8, 2020

(30) Foreign Application Priority Data
Oct. 6, 2017    (AU) .................................. 2017904042

(51) Int. Cl.
*A61Q 19/10*    (2006.01)
*A61K 8/66*    (2006.01)
(Continued)

(52) U.S. Cl.
CPC .................. *A61K 8/66* (2013.01); *A61K 8/39* (2013.01); *A61K 8/4993* (2013.01); *A61K 8/86* (2013.01); *A61Q 19/10* (2013.01); *C12N 9/50* (2013.01)

(58) Field of Classification Search
CPC . A61Q 19/10; A61K 8/46; A61K 8/66; A61K 8/4993; A61K 8/39; A61K 8/86; C12N 9/50
(Continued)

(56) References Cited

U.S. PATENT DOCUMENTS 2,988,488 A    6/1961    Robison et al.
2008/0089854 A1*    4/2008    Whewell ................ A61K 8/375
                                                        424/65

(Continued)

FOREIGN PATENT DOCUMENTS

CN    105543422    *    5/2016
CN    105886488         8/2016
(Continued)

OTHER PUBLICATIONS

English transaltion (Apr. 26, 2022) of the Patent No. CN 105543422 A.*
(Continued)

*Primary Examiner* — Eisa B Elhilo
(74) *Attorney, Agent, or Firm* — Klarquist Sparkman, LLP

(57) ABSTRACT

Provided herein is a method of at least partly removing a biological deposit, such as a dag, from the skin of an animal. The method includes administering to the biological deposit an effective amount of a composition containing a keratinase, and optionally one or both of a reducing agent and a surfactant. Also provided is a composition for use in the aforementioned method as well as a method of making same.

16 Claims, 26 Drawing Sheets

(51) Int. Cl.
    *A61K 8/39* (2006.01)
    *A61K 8/49* (2006.01)
    *A61K 8/86* (2006.01)
    *C12N 9/50* (2006.01)

(58) Field of Classification Search
    USPC .................................................... 424/94.63
    See application file for complete search history.

(56) References Cited

U.S. PATENT DOCUMENTS

2009/0110657 A1* 4/2009 Whewell ................ A61K 8/375
                                                          424/78.07
2015/0208694 A1* 7/2015 Yu ........................ C07K 14/465
                                                          426/657

FOREIGN PATENT DOCUMENTS

| CN | 106282210 | | 1/2017 |
|----|-----------|---|--------|
| GB | 981402 | * | 1/1965 |
| WO | WO 2014/013080 | | 1/2014 |
| WO | WO 2017/087234 | | 5/2017 |

OTHER PUBLICATIONS

Bhange et al., "Simultaneous production of detergent stable keratinolytic protease, amylase and biosurfactant by *Bacillus subtilis* PF1 using agro industrial waste," *Biotechnology Reports*, vol. 10, pp. 94-104, 2016.

\* cited by examiner

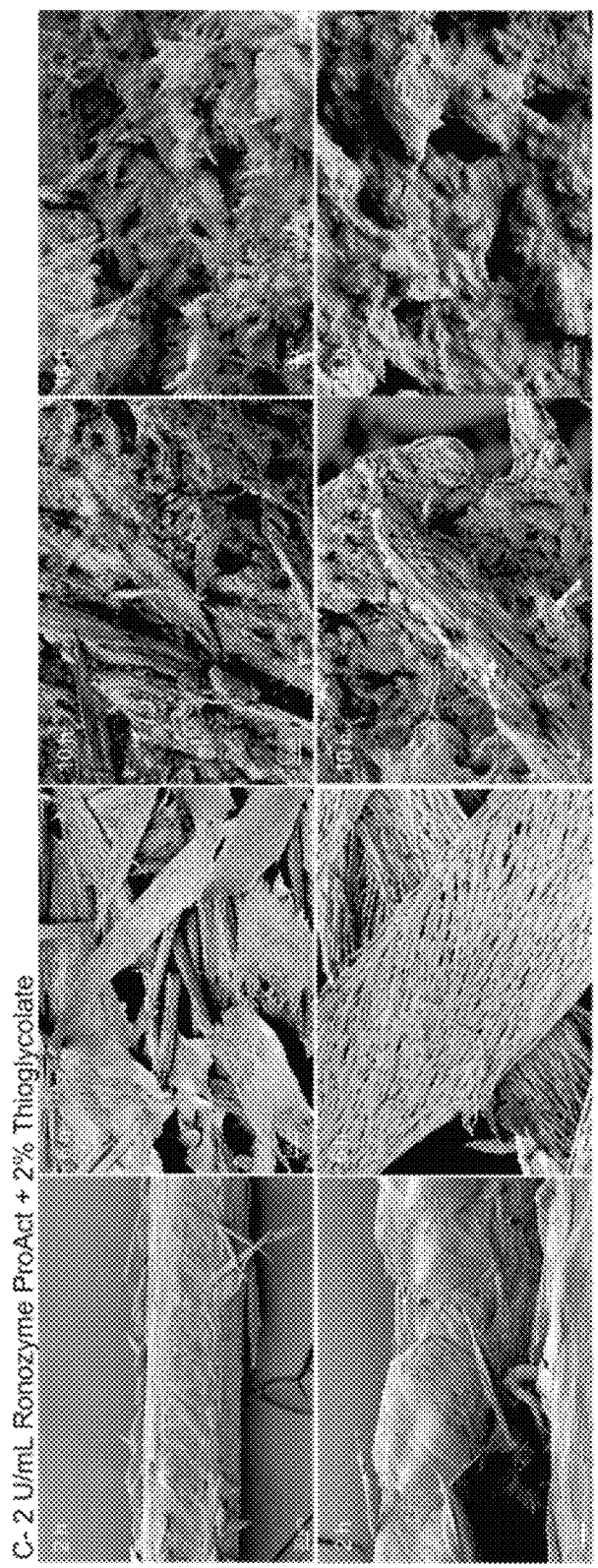
FIG. 7C
FIG. 7D

REMOVAL OF BIOLOGICAL DEPOSITS

CROSS REFERENCE TO RELATED APPLICATIONS

This is the § 371 U.S. National Stage of International Application No. PCT/AU2018/050639, filed Jun. 25, 2018, which was published in English under PCT Article 21(2), which in turn claims the benefit of AU Application No. 2017904042, filed Oct. 6, 2017, which is incorporated herein by reference in its entirety.

TECHNICAL FIELD

THIS INVENTION relates to a method of removing biological deposits, such as dung and dags, from the skin of animals, and more particularly cattle.

BACKGROUND

Dags or manure balls covering cattle hides remain a major issue for the meat and leather industries. Dags are recalcitrant aggregates formed of dung, hair, soil, urine, sugars and straw, and must be removed to reduce the likelihood of microbial meat contamination and irreversible damage during leather processing. Current removal methods typically require extensive hose washing over many hours per animal resulting in high water use, costs and stress to the animal. The problem is aggravated in regions with rainy winter seasons, when animals become wet and muddy.

Dags are mainly composed of lignocellulosic material (cellulose, hemicellulose and lignin) and other minor components, like proteins, including hair keratin, lipids, sugars/starch and minerals (Pauly and Keegstra 2008). Enzymes capable of degrading the constituents of biomass have been implemented in industries such as pulp and paper processing, textiles, food, agriculture and biofuels (Kuhad et al. 2011). The application of enzymes for the degradation of biomass associated with dags has the potential to generate numerous benefits compared to current methods. These benefits include reductions in time, water use, animal stress and the cost of cleaning cattle in an environmentally benign system. In the UK, enzymes have been shown to be effective towards dag removal resulting in patentable technology (Covington and Evans 2003).

Previous investigations into the enzymatic removal of dags in Australia have shown some levels of success, but no enzymatic dag removal method has been implemented so far. Further to this, variability in dag composition may require a specific formulation for the removal of these structures in the Australian cattle. Accordingly, there remains a need for improved methods of removing biological deposits, such as dags from the skin or hides of animals, such as cattle.

SUMMARY

The present invention is broadly directed to a method for removal of biological deposits, such as dags, from the skin of animals by administration of a protease that is capable of degrading keratin thereto. To this end, the protease targets the interaction between the biological deposit and associated hair. Furthermore, the inventors have discovered that the activity or effectiveness of the protease in this manner can be improved by the inclusion of a reducing agent and/or a surfactant.

In a first aspect, the invention provides a method of removing, at least in part, a biological deposit from skin of an animal, including the step of administering to the biological deposit an effective amount of a composition comprising a protease having keratinolytic activity, to thereby remove the biological deposit from the animal.

Suitably, the composition further comprises a reducing agent. Preferably, the reducing agent is or comprises a sulfur containing compound. More preferably, the reducing agent is selected from the group consisting of a sulphite, a thiol, a cysteine and any combination thereof. Even more preferably, the reducing agent is selected from the group consisting of a sulphite salt, a thioglycolate salt and any combination thereof.

Suitably, the composition further comprises a surfactant. In one particular embodiment, the surfactant is or comprises a non-ionic surfactant. In another embodiment, the surfactant is or comprises a wetting agent. Preferably, the surfactant is selected from the group consisting of an alkylphenol ethoxylate, a saponin, an isotridecanol polyglycol ether, a polyoxyethylene alkyl ether, and any combination thereof. In particular embodiments, the polyoxyethylene alkyl ether is or comprises a polyoxyethylene octyl phenyl ether, a polyoxyethylene (20) cetyl ether or any combination thereof.

In certain embodiments, the method of the present aspect further includes the step of washing the biological deposit.

In a second aspect, the invention provides a composition for removing, at least in part, a biological deposit from skin of an animal, comprising a protease having keratinolytic activity and one or both of a reducing agent and a surfactant.

Suitably, the reducing agent is or comprises a sulfur containing compound. Preferably, the reducing agent is selected from the group consisting of a sulphite, a thiol, a cysteine and any combination thereof. More preferably, the reducing agent is selected from the group consisting of a sulphite salt, a thioglycolate salt and any combination thereof.

Suitably, the surfactant is or comprises a non-ionic surfactant. In particular embodiments, the surfactant is selected from the group consisting of an alkylphenol ethoxylate, a saponin, an isotridecanol polyglycol ether, a polyoxyethylene alkyl ether, and any combination thereof. Preferably, the polyoxyethylene alkyl ether is or comprises a polyoxyethylene octyl phenyl ether, a polyoxyethylene (20) cetyl ether or any combination thereof.

In one embodiment, the surfactant is or comprises a wetting agent.

Suitably, the composition is for use in the method of the first aspect.

Regarding the aforementioned aspects, the composition suitably further comprises one or more of an amylase, a cellulase, a xylanase and a laccase.

In a third aspect, the invention provides a method of preparing a composition for removing, at least in part, a biological deposit from a portion of skin of an animal, said method including the step of mixing a protease having keratinolytic activity and one or both of a reducing agent and a surfactant, to thereby prepare the composition.

Suitably, the composition is that of the second aspect.

In respect of the first, second and third aspects, the biological deposit suitably is or comprises animal faeces. Preferably, the biological deposit is or comprises cattle dung.

In one embodiment of the aforementioned aspects, the animal is a live animal.

Referring to the first, second and third aspects, the species of animal is suitably bovine.

As used herein, except where the context requires otherwise, the term "comprise" and variations of the term, such as "comprising", "comprises" and "comprised", are not intended to exclude further elements, components, integers or steps but may include one or more unstated further elements, components, integers or steps.

It will be appreciated that the indefinite articles "a" and "an" are not to be read as singular indefinite articles or as otherwise excluding more than one or more than a single subject to which the indefinite article refers. For example, "a" cell includes one cell, one or more cells and a plurality of cells.

BRIEF DESCRIPTION OF THE DRAWINGS

By way of example only, embodiments of the invention are described more fully hereinafter with reference to the accompanying drawing, in which: —

FIG. 1A) Hair treated with 0.2, 1 or 2 U/mL of Multifect PR 6 L or Cibenza DP100 at pH 8, or 0.02, 0.1 and 0.2 U/mL of Ronozyme ProAct at pH 10. The control is defined as hair samples treated in buffer solution only at pH 8 or pH 10. Values represent the load in Newtons required for hair to break. * Significant statistical difference with control sample (p<0.01). FIG. 1B) Load vs extension curves for the control, 2 U/mL Multifect PR 6L, 2 U/mL Cibenza DP100 and 0.2 U/mL Ronozyme ProAct treated hair samples. The end point of each curve represents the force at the point of hair breakage.

FIG. 2A) Hair samples treated with 0.2, 1 or 2 U/mL Ronozyme ProAct or Cibenza DP100 for 16 hours at 37° C. with or without reducing agents. The extent of hair degradation can be seen by the disappearance of the hair fibre and the increased colouration of the solution, presumably due to melanin release from the brown hair. FIG. 2B) Soluble peptides after hair treatment with 0.2, 1 or 2 U/mL of Cibenza DP100 or Ronozyme ProAct for 16 hours at 37° C. in the presence of reducing agents. The control is defined as hair sample treated in buffer solution without enzyme.

FIGS. 7A-7D: Feathers treated with 2 U/mL Ronozyme ProAct without reducing agent (FIG. 7A), with 1% sodium sulfite (FIG. 7B) or with 2% sodium thioglycolate (FIG. 7C) for 2, 6, 10 and 16 hours at 37° C. and control (FIG. 7D). Two different images and magnifications (higher magnification in the lower row) are shown for each time and treatment.

FIG. 8A) Untreated dag samples. FIG. 8B) Treated dag samples with 10 U/mL Spezyme LT 300, 10 U/mL Accellerase 1500 and 10 U/mL Multigrain Ronozyme with Triton X-100 5% (1), Saponin 5% (2), Brij58 5% (3), without surfactant (4) and with 10 U/mL of Laccase (5). Control sample without enzymes or surfactant (6). Specific dag samples in A are different from dag samples in B. Photos in B were taken after spatula testing.

DETAILED DESCRIPTION

Figure 1A:
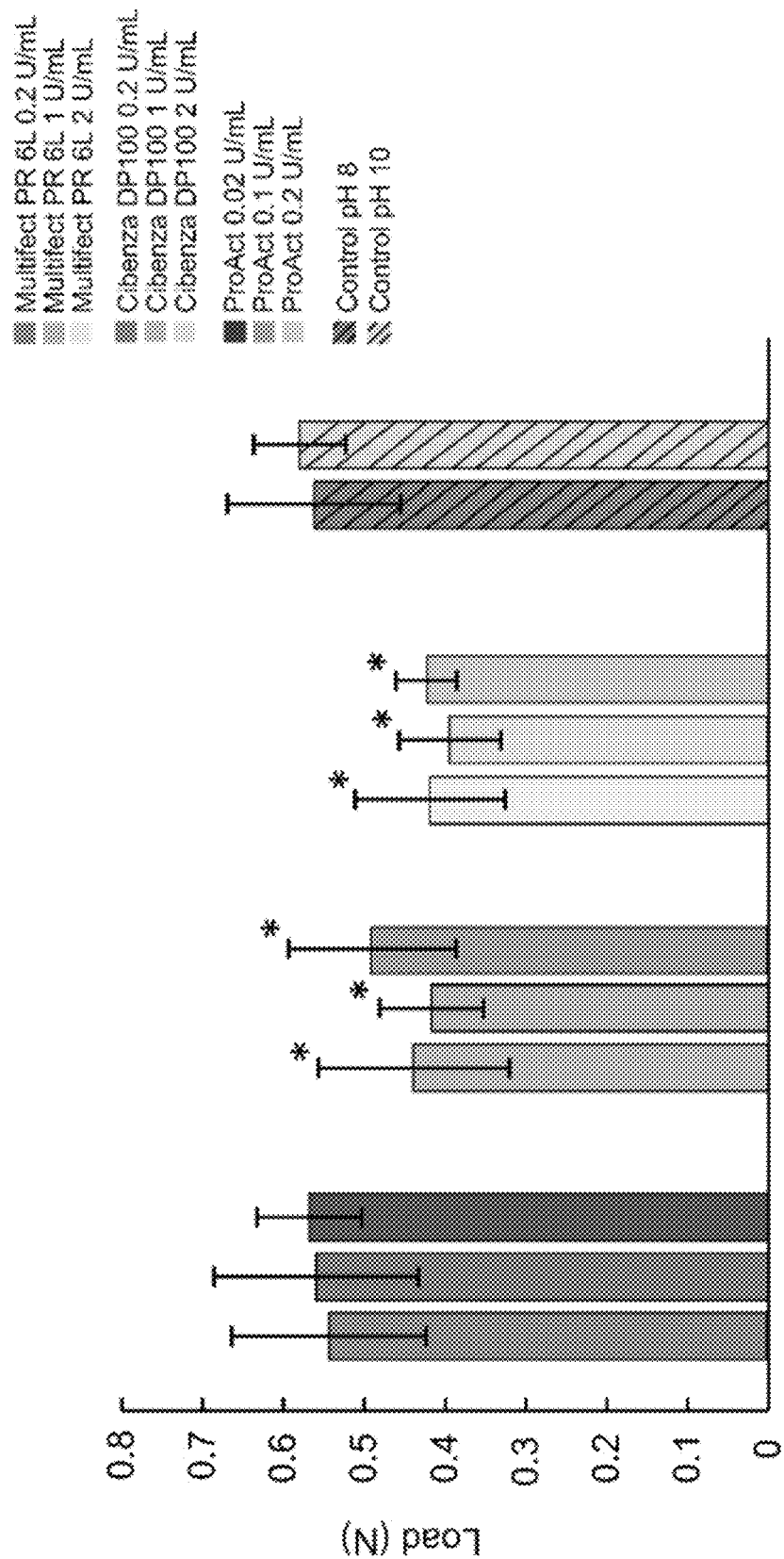
FIGS. 1A and 1B.

The present invention is predicated, at least in part, on the surprising discovery that proteases, and in particular those demonstrating keratinolytic activity, which appear to target the interaction between the dag and the hair, were effective in dag degradation by weakening the framework of hairs and grain protein holding the structure together.

Accordingly, in one aspect, the invention provides a method of removing, at least in part, a biological deposit from a portion of skin of an animal, including the step of administering to the biological deposit an effective amount of a composition comprising a protease having keratinolytic activity, to thereby remove the biological deposit from the animal.

Suitably, the protease having keratinolytic activity acts on protein components and/or a keratinous structures, such as hair, associated with the biological deposit and/or skin, to facilitate removal of the biological deposit therefrom.

It will be appreciated that the biological deposit described herein may include, for example, faeces, hair, soil, urine, sugars/starch, lignocellulosic material (i.e., cellulose, hemicellulose and lignin), such as grass, straw and silage, proteins, such as that from feed grain, and lipids. In one preferred embodiment, the biological deposit suitably is or comprises animal faeces, such as cattle dung, and as such may be or include dags or manure balls. To this end, dags or manure balls are normally attached to animal hides through hair alone and adherence of the dag to the epidermis is not observed (Covington et al. 1999). Without being bound by any theory, the protease having keratinolytic activity is administered to target not only the hair component of the dag or manure ball at the point of attachment to the skin of the animal, but also internally within the dag or manure ball. Accordingly, these proteases can selectively weaken or remove the hair at the attachment site of the biological deposit as well as potentially aid the access of any biomass degrading enzymes to the site of the dag-hair interaction. Additionally, protein from partially digested grain or feed material could also function as an adhesive or glue within the dag or manure ball, acting to bind, at least in part, the other components together. This protein component of the dag or manure ball may also be degraded by the protease having proteolytic activity or keratinase.

As generally used herein, the term "protease" refers to enzymes which are capable of hydrolysing proteins, polypeptides and/or peptides by cleavage of the peptide bond that links amino acids together. Proteases can also be referred to, for example, as peptidases, such as exo- and endo-peptidases, proteinases, peptide hydrolases, or proteolytic enzymes.

The term "protease" further includes naturally-occurring and synthetic proteolytic enzymes, as well as protease variants and derivatives thereof. It also comprises any fragment of a proteolytic enzyme, and variants engineered by insertion, deletion, recombination and/or any other method, that leads to proteases that differ in their amino acid sequence from the naturally-occurring protease or the protease variants. It also comprises protein molecules with posttranslational and/or chemical modifications, e.g. Glycosylation, PEGylation, HESylation, gamma carboxylation and acetylation, any molecular complex or fusion protein comprising one of the aforementioned proteins.

The terms "protease having keratinolytic activity" or "keratinase" refers to an enzyme that hydrolyzes, at least in part, the protein keratin. It is generally recognised that the keratinolytic process involves two steps, sulfitolysis and proteolysis (Yamamura 2002, Grumbt 2013). During sulfitolysis, cleavage of disulfide bonds changes the conformation of keratins such that more sites for keratinase action can be exposed (Vignardet 2001).

Keratin is an insoluble protein having cross-linked disulphide, hydrogen and hydrophobic bonds which is present in the skin where it forms protective structures often found in epidermic appendages such as wool, hair ($\alpha$-keratin) and feathers ($\beta$-keratin). Based on their secondary structure, keratins are generally classified into $\alpha$-keratin and $\beta$-keratin. $\beta$-Keratin is rich in $\beta$-pleated sheets (Meyers et al. 2008) and is constructed from supramolecular fibril bundles (Bodde et al. 2011), and $\alpha$-keratin consists of $\alpha$-helical-coil coils, which are self-assembled into intermediate filaments (Meyers et al. 2008, McKittrick et al. 2012). Keratins contain a high degree of cysteine which confers rigidity and chemical resistance via the crosslinking of disulfide bonds. $\alpha$-keratin has a higher degree of disulfide bonds than $\beta$-keratin which makes it more compact and resistant to degradation by enzymes. Almost all keratinaceous materials, like feathers, hair, bristles and wool, possess different amounts of $\alpha$- and $\beta$-keratins.

Proteases having keratinolytic activity are largely serine or metallopeptidases, which generally attack the peptide bonds of the keratin substrate. It will be appreciated, however, that these proteolytic enzymes can have a wide range of substrate specificity, such that in addition to keratin, the protease having keratinolytic activity can also degrade other proteins, such as fibrin, elastin, collagen, casein, bovine serum albumin and gelatin. The protease having keratinolytic activity or keratinase may be any known in the art, such as those that have been studied from various groups of bacteria and fungi (Lin et al. 1992, Riffel et al. 2007, Brandelli et al. 2010, Jeong et al. 2010, Cavello et al. 2012, Jaouadi et al. 2013, Gegeckas et al. 2015, Huang et al. 2015). It will further be appreciated that common proteases like pepsin and papain are generally not capable of degrading keratin. (Brandelli 2006).

Methods of determining the keratinolytic activity of proteases are well known in the art, and include, for example, spectrophometric analyses using azo-keratin, keratin azure, guinea pig hair, feathers and other keratin structures, although reference is made to examples of such techniques as provided in Chapter 10 of METHODS TO DETERMINE ENZYMATIC ACTIVITY, Eds Vermelho and Couri, 2013 (Bentham Science Publishers).

Proteases having keratinolytic activity or keratinases are typically produced by certain fungi, actinobacteria and bacteria, when in the presence of keratin-containing substrate. To this end, the protease having keratinolytic activity can be derived or isolated, at least in part, from such microorganisms known in the art capable of producing such a protease. In particular embodiments, the protease having keratinolytic activity is derived or isolated, at least in part, from a microorganism of the genus selected from the group consisting of *Nocardiopsis* spp., *Bacillus* spp. (e.g., *B. licheniformis, B. pumilus, B. subtilis, B. cereus*), *Vibrio* spp., *Streptomyces* spp. (e.g., *S. pactum, S. albus*), *Aspergillus* spp., *Rhizomucor* spp., *Trichophyton* spp. (e.g., *T. mentagrophytes, T. rubrum, T. gallinae*), *Microsporum* spp. (e.g., *M. canis, M. gypseum*), *Staphylococcus* (e.g., *S. aureus*), *Doratomyces* spp. (e.g., *D. micrsoporus*), *Paecilomyces* spp. (e.g., *P. marquandii*), *Fervidobacterium* spp. (e.g., *F. pennivorans*) and any combination thereof. In particularly preferred embodiments, the protease having keratinolytic activity is derived from *Nocardiopsis prasina* (e.g., Ronozyme ProAct), *Bacillus licheniformis* (e.g., Cibenza DP100, Multifect PR 6L) and any combination thereof.

The protease having keratinolytic activity is suitably present in the composition in an amount of at least about 0.25% to about 15% (e.g., about 0.25%, 0.5%, 0.75%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, 10%, 10.5%, 11%, 11.5%, 12%, 12.5%, 13%, 13.5%, 14%, 14.5%, 15%) by weight of the composition. Preferably, the protease having keratinolytic activity is present in an amount ranging between about 0.5% to about 5% by weight of the composition.

Further to the above, the protease having keratinolytic activity is suitably present in the composition in an amount or concentration of at least about 0.1 U/mL to about 20 U/mL (e.g., about 0.1, 0.25, 0.5, 0.75, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20 U/mL or any range therein). It will be appreciated that a measure of protease (i.e., keratinase) units will depend, at least in part, upon the particular protease having keratinolytic activity and/or the specific assay used to determine keratinase enzyme activity. By way of example and as provided hereinafter, for the keratin azure assay, one unit of keratinase activity is defined as the amount of enzyme or protease causing an increase of 0.1 in absorbance at 440 nm after incubation for 30 min at 37° C. Given the above, however, alternative methods of determining keratinase enzymatic activity are contemplated.

Preferably, the protease having keratinolytic activity or keratinase of the present invention has been at least substantially purified. For the purposes of this invention, by "purified" or "substantially purified" is meant the protease has been removed from its natural state (e.g., purified from bacteria or fungi) or otherwise been subjected to human manipulation. Purified material may be substantially or essentially free from components that normally accompany it in its natural state, or may be manipulated so as to be in an artificial state together with components that normally accompany it in its natural state. The term "purified" also encompasses terms such as "enriched" and "isolated". Preferably, the protease of the invention is at least about 80% pure, more preferably at least about 90% pure, and even more preferably at least about 99% pure.

Suitably, the biological deposit is contacted with the composition for a period of time sufficient to for the protease having keratinolytic activity to, at least partly, degrade or hydrolyse a portion of keratin (e.g., hair) associated with the skin and/or biological deposit of the animal. For the purpose of description, reference is made to a range of 5 to 600 minutes (e.g., 5, 10, 15, 20, 25, 30, 35, 40, 45, 50, 55, 60, 70, 80, 90, 100, 110, 120, 130, 140, 150, 160, 170, 180, 190, 200, 220, 240, 260, 280, 300, 320, 340, 360, 380, 400, 420, 440, 460, 480, 500, 520, 540, 560, 580, 600 minutes and any range therein), but contact times may be shorter, such as 1 minute, or longer, such as 1000 minutes.

As used herein, "administering" or "administration" may refer to, for example, contacting, soaking, impregnating, spraying, suspending, immersing, saturating, dipping, wetting, rinsing, washing, submerging, and/or any variation and/or combination thereof.

In this context of the present invention, "effective amount" is meant an amount or concentration of the composition described herein sufficient to elicit the desired chemical and/or physicochemical effect/s on the biological deposit, so as to promote or enhance the at least partial removal of said biological deposit from skin of the animal. Thus, an effective amount of the composition is an amount sufficient to contact and degrade or hydrolyse, for example, a sufficient amount of the keratin in a sufficient portion of hair associated with the biological deposit so as to facilitate or promote removal therefrom.

The effective amount can vary, depending upon factors such as the age, breed, species, body weight, fertility and general health of the animal, the composition of the biological deposit, the make up of the composition and the manner in which it is to be administered thereto.

Suitably, the biological deposit is further contacted or treated with a reducing agent. The terms "reducing agent", "reductant" or "reducer" as generally used herein refer to an agent, element or compound in a reduction-oxidation (redox) reaction that donates an electron to another species. Accordingly, a reducing agent will be oxidised in a redox reaction. Without wishing to be bound by any theory, it is thought that the presence of a reducing agent may stimulate or promote keratin degradation by the protease having keratinolytic activity. To this end, reducing agents may breakdown disulphide bonds present in keratin, opening up the structure to aid hydrolysis by the protease having keratinolytic activity.

Suitably, the reducing agent may be administered to the biological deposit prior to, during and/or after the step of administering the protease with keratinolytic activity. Accordingly, the method of the present aspect may include the further step of administering an effective amount of a reducing agent to the biological deposit. More preferably, the composition further comprises the reducing agent and, as such, the protease having keratinolytic activity and the reducing agent are administered simultaneously.

In one embodiment, only one reducing agent is used in combination with the protease of the present invention. In another embodiment, any combination of two or more (e.g., 2, 3, 4, 5, 6, 7, 8, 9, or 10) reducing agents are used.

It will be understood that the reducing agent may be any as are well known in the art. Suitably, the reducing agent is a sulfur-containing agent or compound (e.g., includes a sulfur containing moiety). By way of example, the reducing agent may include a sulphite (e.g. $Na_2SO_3$ and $NaHSO_2$), a thiol, a cysteine, a bisulfite, a dithionite, a metabisulfite, sulphur dioxide, DTT, β-mercaptoethanol and a sulphide. Preferably, the reducing agent is selected from the group consisting of a sulphite, a thiol, a cysteine and any combination thereof. More preferably, the reducing agent is selected from the group consisting of a sulphite salt, a thioglycolate salt and any combination thereof. Even more preferably, the reducing agent is selected from the group consisting of sodium sulphite, sodium thioglycolate and any combination thereof.

The reducing agent is suitably present in the composition in an amount of at least about 0.25% to about 10% (e.g., about 0.25%, 0.5%, 0.75%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, 10% and any range therein) by weight of the composition. Preferably, the reducing agent is present in an amount ranging between about 0.5% to about 5% by weight of the composition.

For the method of the present aspect, the biological deposit is suitably further contacted or treated with a surfactant. As used herein, the term "surfactant" or "surface-active agent" refers to an agent, usually an organic chemical compound that is at least partially amphiphilic (i.e., typically containing a hydrophobic tail group and hydrophilic polar head group). Given their structure, surfactants are generally capable of lowering the surface tension (or interfacial tension) between two liquids or between a liquid and a solid. Further to this, these properties typically allow solubility of the surfactant in organic solvents as well as in water, and allow the surfactant to promote solubilization or at least dispersal of fatty/waxy materials in water and water-containing solutions. In this regard, a surfactant may act as a detergent, a wetting agent, an emulsifying agent, a foaming agent and/or a dispersing agent. In one particularly preferred embodiment, the surfactant of the present invention is or comprises a wetting agent.

Suitably, the surfactant may be administered to the biological deposit prior to, during and/or after the step of administering the composition comprising the protease with keratinolytic activity thereto. Accordingly, the method of the present aspect may include the further step of administering an effective amount of a surfactant to the biological deposit. More preferably, the composition further comprises the surfactant and, as such, the protease having keratinolytic activity and the surfactant are administered simultaneously to the biological deposit.

The surfactant is suitably present in the composition in an amount of at least about 1% to about 20% (e.g., about 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, 10%, 10.5%, 11%, 11.5%, 12%, 12.5%, 13%, 13.5%, 14%, 14.5%, 15%, 15.5%, 16%, 16.5%, 17%, 17.5%, 18%, 18.5%, 19%, 19.5%, 20% and any range therein) by weight of the composition. Preferably, the surfactant is present in an amount ranging between about 2% to about 10% by weight of the composition.

In one embodiment, a single surfactant is used in combination with the protease of the present invention. In another embodiment, any combination of two or more (e.g., 2, 3, 4, 5, 6, 7, 8, 9, or 10) surfactants are used.

For the present invention, the surfactant may be any as are well known in the art and may include, for example, a non-ionic surfactant, an anionic surfactant, a cationic surfactant, a zwitterionic surfactant, a cation-anion composite surfactant and any combination thereof. In one particular embodiment, the surfactant is or comprises a non-ionic surfactant.

Preferably, the surfactant is selected from the group consisting of an alkylphenol ethoxylate, a saponin, an isotridecanol polyglycol ether (e.g., Genapol X-80 (i.e., Isotridecyl alchohol polyglycol ether (8EO), Oligoethylene glycol monoalkyl ether, Polyethylene glycol monoalkyl ether)), a polyoxyethylene alkyl ether (e.g., Triton-X 100 (i.e., 4-(1,1,3,3-Tetramethylbutyl)phenyl-polyethylene glycol, t-Octylphenoxypolyethoxyethanol, Polyethylene glycol tert-octylphenyl ether); Brij-58 (i.e., Polyethylene glycol hexadecyl ether, Polyoxyethylene (20) cetyl ether)), and any combination thereof. In particular embodiments, the polyoxyethylene alkyl ether is or comprises a polyoxyethylene octyl phenyl ether, a polyoxyethylene (20) cetyl ether or any combination thereof.

In one embodiment, the composition comprises one or a plurality of further enzymes. Non-limiting examples of further enzymes include an amylase (e.g., alpha-amylase), a cellulase, a xylanase, a laccase, a further protease, a lipase, a urease, a uricase, a pectinase and a ligninase. In this respect, it will be appreciated that a biological deposit, such as a dag or manure ball, may be removed more efficiently and effectively from skin of the animal by enzymatically targeting one or more of the components, such as lignocellulose, starch, lipid and/or protein, thereof with such specifically acting enzymes.

It will be appreciated that the composition described herein may further comprise one or more carriers, diluents or excipients, as are known in the art. By way of example, these carriers may be selected from a group including sugars, starches, cellulose and its derivatives, malt, gelatine, talc, calcium sulfate, liposomes and other lipid-based carriers, vegetable oils, synthetic oils, polyols, alginic acid, phosphate buffered solutions, emulsifiers, isotonic saline and salts such as mineral acid salts including hydrochlorides, bromides and sulfates, organic acids such as acetates, propionates and malonates and pyrogen-free water. Suitably, the carriers, diluents or excipients are not detrimental or harmful to the skin of the animal to which the composition is to be added.

In this respect, the composition of the present invention is preferably pharmaceutically compatible or acceptable for topical administration to the animal. Such compositions may be prepared by any of the methods of pharmacy but all methods include the step of bringing into association one or more agents as described above with the carrier which constitutes one or more necessary ingredients. In general, the compositions can be prepared by uniformly and intimately admixing the agents of the invention with liquid carriers or the like.

A useful reference describing pharmaceutically acceptable carriers, diluents and excipients is Remington's Pharmaceutical Sciences (Mack Publishing Co. N.J. USA, 1991), which is incorporated herein by reference.

In certain embodiments, the method of the present aspect further includes the step of washing the biological deposit after administration of the composition provided herein so as to, at least partly, facilitate removal of the biological deposit from the skin of the animal. In this regard, washing may be carried out with a wash solution and/or water. The biological deposit may be washed with water and/or a wash solution one or more times, such as 2, 3, 4, or more times.

With regards to the invention of the present aspect, such a method can be performed either ex vivo on skin previously removed from the animal or in vivo on skin of a live animal. Preferably, the method is performed in vivo on a live animal, such as cattle. It is also to be understood that such removal of the biological deposit from skin of the animal need not be absolute to be beneficial to, for example, downstream processing of the animal for meat and/or hide production.

Accordingly, in particular embodiments, the method of the present aspect removes from the skin of the animal at least 25% (e.g., 25%, 30%, 35%, 40%, 45%, 50%, 55%, 60%, 65%, 70%, 75%, 80%, 85%, 90%, 95%, 100% or any range therein) of the biological deposited treated or contacted with the composition described herein, more preferably at least 50% of the biological deposit treated or contacted therewith, and even more preferably at least 70% or greater of the biological deposit treated or contacted therewith.

In a further aspect, the invention provides a composition for removing, at least in part, a biological deposit from a portion of skin of an animal, comprising a protease having keratinolytic activity and one or both of a reducing agent and a surfactant.

Suitably, the reducing agent is selected from the group consisting of a sulphite, a thiol, a cysteine and any combination thereof. Preferably, the reducing agent is selected from the group consisting of a sulphite salt, a thioglycolate salt and any combination thereof. More preferably, the reducing agent is selected from the group consisting of sodium sulphite, sodium thioglycolate and any combination thereof.

In particular embodiments, the surfactant is selected from the group consisting of an alkylphenol ethoxylate, a saponin, an isotridecanol polyglycol ether, a polyoxyethylene alkyl ether, and any combination thereof. Preferably, the polyoxyethylene alkyl ether is or comprises a polyoxyethylene octyl phenyl ether, a polyoxyethylene (20) cetyl ether or any combination thereof.

The composition of the present aspect suitably further comprises one or a plurality of further enzymes, such as those herein before described. More preferably, the composition further comprises one or more of an amylase, a cellulase, a xylanase and a laccase.

Suitably, the biological deposit is or comprises animal faeces. Preferably, the biological deposit is or comprises cattle dung.

In one embodiment, the animal is a live animal.

In particular embodiments, the composition further comprises one or more carriers, diluents or excipients, such as those hereinbefore described.

In a related aspect, the invention provides a method of preparing a composition for removing, at least in part, a biological deposit from a portion of skin of an animal, said method including the step of mixing a protease having keratinolytic activity and one or both of a reducing agent and a surfactant, to thereby prepare the composition.

Suitably, the reducing agent is selected from the group consisting of a sulphite, a thiol, a cysteine and any combination thereof. Preferably, the reducing agent is selected from the group consisting of a sulphite salt, a thioglycolate salt and any combination thereof. More preferably, the reducing agent is selected from the group consisting of sodium sulphite, sodium thioglycolate and any combination thereof.

In particular embodiments, the surfactant is selected from the group consisting of an alkylphenol ethoxylate, a saponin, an isotridecanol polyglycol ether, a polyoxyethylene alkyl ether, and any combination thereof. Preferably, the polyoxyethylene alkyl ether is or comprises a polyoxyethylene octyl phenyl ether, a polyoxyethylene (20) cetyl ether or any combination thereof.

The method of the present aspect suitably further comprises further admixing one or a plurality of further enzymes, such as those herein before described, into the composition. Preferably, the composition further comprises one or more of an amylase, a cellulase, a xylanase and a laccase.

Suitably, the biological deposit is or comprises animal faeces. Preferably, the biological deposit is or comprises cattle dung.

In one embodiment, the animal is a live animal.

In particular embodiments, the method further comprises admixing one or more carriers, diluents or excipients, such as those hereinbefore described, into the composition.

The methods described herein may be applicable to any animal, including humans and non-human animals, such as avians inclusive of poultry (e.g., chickens, ducks, geese, pigeons, quails and turkeys), ruminants (e.g., cattle, sheep, goats etc), pigs, horses, donkeys, dogs and cats. Preferably, the animal is bovine.

Throughout the specification the aim has been to describe the preferred embodiments of the invention without limiting the invention to any one embodiment or specific collection of features. It will therefore be appreciated by those of skill in the art that, in light of the instant disclosure, various modifications and changes can be made in the particular embodiments exemplified without departing from the scope of the present invention.

The reference to any prior art in this specification is not, and should not be taken as, an acknowledgement or any form of suggestion that the prior art forms part of the common general knowledge.

All computer programs, algorithms, patent and scientific literature referred to herein is incorporated herein by reference.

So that the present invention may be more readily understood and put into practical effect, the skilled person is referred to the following non-limiting examples.

EXAMPLE 1

In the present Example, the enzymatic degradation of hair and feathers using commercially available proteases and the effects of two common reducing agents, sodium sulfite and sodium thioglycolate were studied. While sodium sulfite is a known abiotic component of microbial keratin degradation (Grumbt 2013), sodium thioglycolate has been extensively used in hair cosmetic products for waving or straightening. We have shown that the presence of reducing agent is crucial for complete hair and feather degradation by keratinases and proposed that the specific activity of keratinases could, in part, be related to substrate absorption capability of the enzyme. Interestingly, *Nocardiopsis prasina* keratinase (Ronozyme ProAct) showed greater decomposition capacity than *B. licheniformis* PWD-1 keratinase (Cibenza DP100) from the commercial products tested. Since Ronozyme ProAct has not been previously marketed as a keratinase, the results from this work open a new application ground for this product. Time point analysis of enzymatic treated hair and feathers using scanning electron microscopy (SEM) revealed well-defined stages of keratin decomposition, bringing insight into the process of keratin degradation by proteases.

Material and Methods

Protease Activity Determination

Azocasein was used as substrate for protease activity determination (Caldas et al. 2002). 50 µL of diluted enzyme solution was added to 50 µL of 2% azocasein in 100 mM Tris-HCl, pH 8 and incubated at 37° C. for 30 min. Non-digested azocasein was precipitated by addition of 100 µL of 10% trichloroacetic acid (TCA) to each incubation, kept on ice for 10-15 min and centrifuged at 4,500×g for 10 min at room temperature. 100 µL of supernatant was transferred to a 96-well microtitre plate containing 200 µL of 1 M NaOH and the absorbance was measured at 440 nm. Determinations for each enzyme dilution were performed in triplicate. Negative controls were prepared by precipitating the azocasein substrate with TCA and followed by addition of the enzyme dilution without incubation. Increased absorbance indicates the presence of proteolytic activity. One azocasein unit was defined as an increase of 0.1 absorption units after incubation for 30 min at 37° C.

Keratinase Activity Determination

Keratinolytic activity was determined using keratin azure (Sigma Aldrich) as a substrate following the manufacturer's instructions with some modifications. Briefly, 100 µL of enzyme dilution was added to 0.01 g of keratin azure in 2.4 mL of 100 mM Tris-HCl buffer pH 8 or pH 10. Samples were incubated at 37° C. for 1 h at 200 rpm. After incubation, samples were centrifuged at 4500×g for 10 min and the absorbance of the clarified supernatants was determined at 595 nm. Determinations for each enzyme dilution were performed in triplicate. For the negative control, 0.01 g of keratin azure in 2.5 mL of reaction buffer was incubated at 37° C. for 1 h with shaking at 200 rpm and the absorbance was measured at 595 nm. One unit was defined as the amount of enzyme causing an increase of 0.1 in absorbance at 440 nm after incubation for 30 min under the experimental conditions described. For keratinolytic activity determination in presence of reducing agents, the keratin azure assay was performed as indicated with the addition of 1 or 2% of sodium sulfite or 1, 2 or 5% of sodium thioglycolate.

Hair Force to Break Studies

Hair samples from cow hides (*Bos taurus*) were treated with 0.2, 1 or 2 U/mL of Multifect PR 6L or Cibenza DP100 in 5 mL of 100 mM Tris-HCl buffer pH 8, and 0.02, 0.1 and 0.2 U/mL of Ronozyme ProAct in 5 mL of 100 mM Tris-HCl buffer pH 10, for 16 hours at 37° C. at 200 rpm. Control hair samples were incubated in reaction buffer without enzyme for 16 hours at 37° C. at 200 rpm. A MTS Microforce Tryton 250 force meter was used for axial force testing studies. Dry hair samples of 4 cm length were loaded into two horizontally aligned clamps and displaced 20 mm in a time lapse of 40 s (0.5 mm/s strain rate) for breakage testing at room temperature and ambient relative humidity (~50%). Hair force to break was defined as the load in Newtons required for hair rupture.

Determination of Soluble Peptides after Hair or Feather Treatment

Hair samples from cattle hides (*Bos taurus*) or chicken feathers (*Gallus gallus*), were treated with Cibenza DP100 or Ronozyme ProAct in 5 mL of 100 mM Tris-HCl buffer pH 8 or pH 10, respectively, for 16 hours at 37° C. at 200 rpm. When indicated, 1% sodium sulfite or 2% sodium thioglycolate was added. Control hair and feather samples were incubated in reaction buffer without enzyme for 16 h at 37° C. at 200 rpm. Reducing agent was added when indicated. Soluble peptides were quantified by Bradford assay after 2, 6, 10 and 16 hours of incubation (Bradford 1976).

Scanning Electron Microscopy

Hair and feather samples treated with Cibenza DP100 and Ronozyme ProAct for 2, 6, 10 and 16 hours at 37° C., with or without reducing agent (1% sodium sulfite or 2% sodium thioglycolate), were air dried, fixed in a sample holder stub and gold coated using Leica EM SCD005 Gold Coater (~10 nm). Secondary electron images were obtained with Zeiss Sigma Field Emission Scanning Electron Microscope. Images were obtained under vacuum using 2 kV accelerating voltage.

Results

Enzymatic Activity of Commercial Proteases

Commercial proteases for this study were obtained from different companies, Cibenza DP100 from Novus, Ronozyme ProAct from DSM-Novozymes, Multifect PR 6L from Dupont, Alcalase 2.4 LT, Neutrase 0.8 BrewQ and Flavourzyme from Novozymes (Table 1). These products are commercialised as feed additive (Cibenza DP100 and Ronozyme ProAct) or as proteases for industrial food manufacturing processes (Multifect PR 6L, Alcalase 2.4 LT, Neutrase 0.8 BrewQ and Flavourzyme). Cibenza DP100 is the only product previously shown to have keratinolytic activity (Wang 2011).

TABLE 1

Commercial enzymes used in this study.

| Product Name | Enzyme type(s) | Enzyme source organism | Company |
| --- | --- | --- | --- |
| Cibenza DP100 | Protease | *B. licheniformis* PWD-1 | Novus |
| Alcalase 2.4 L FG | Protease (Subtilisin) | *B. licheniformis* | Novozymes |
| Neutrase 0.8 L BrewQ | Protease | *B. amyloliquefaciens* | Novozymes |
| Flavourzyme | Aminopeptidase | *Aspergillus oryzae* | Novozymes |
| Multifect PR 6L | Protease (Subtilisin) | *B. licheniformis* | Dupont |
| Ronozyme ProAct | Protease | *Nocardiopsis prasina* | DSM/Novozymes |

Protease and keratinase activities of each enzyme were determined by azocasein and keratin azure assays respectively (Table 2). The commercial products Cibenza DP100, Ronozyme ProAct and Multifect PR 6L all showed keratinolytic activity, while Alcalase 2.4 LT, Neutrase 0.8 BrewQ and Flavourzyme showed no keratinolytic activity under the experimental conditions tested (Table 2). Keratinase activity of Cibenza DP100, Ronozyme ProAct and Multifect PR 6L was assayed at pH 8 and 10 to determine best activity condition for further experiments. Only Ronozyme ProAct showed improved activity at pH 10 (Table 2).

TABLE 2

Protease and keratinase activities of commercial enzymes as determined by azocasein and keratin azure assays, respectively.

| Enzyme | Activity | pH | Specific Activity ($10^3$ U/g of protein) |
| --- | --- | --- | --- |
| Cibenza DP100 | Protease | 8 | 10801 ± 788 |
|  | Keratinase | 8 | 16 ± 1 |
|  |  | 10 | 13 ± 1 |
| Ronozyme ProAct | Protease | 8 | 120127 ± 12578 |
|  | Keratinase | 8 | 178 ± 13 |
|  |  | 10 | 262 ± 5 |
| Multifect PR 6L | Protease | 8 | 11 ± 1 |
|  | Keratinase | 8 | 0.132 ± 0.02 |
|  |  | 10 | 0.331 ± 0.06 |
| Alcalase 2.4 LT | Protease | 8 | 11599 ± 2530 |
|  | Keratinase | 8 | 0 ± 0 |
|  |  | 10 | 0 ± 0 |
| Neutrase 0.8 BrewQ | Protease | 8 | 7094 ± 571 |
|  | Keratinase | 8 | 0 ± 0 |
|  |  | 10 | 0 ± 0 |
| Flavourzyme | Protease | 8 | 3949 ± 508 |
|  | Keratinase | 8 | 0 ± 0 |
|  |  | 10 | 0 ± 0 |

For the azocasein assay, unit of enzyme activity is defined as an increase of 0.1 absorption units after incubation for 30 min at 37° C. For keratin azure assay, one unit of enzyme activity is defined as the amount of enzyme causing an increase of 0.1 in absorbance at 440 nm after incubation for 30 min at 37° C.

Mechanical Properties of Enzymatically Treated Hair

Multifect PR 6L, Cibenza DP100 and Ronozyme ProAct, the enzymes shown to have keratinolytic activity (Table 2), were applied to hair samples from cattle hides. Hairs were incubated with 0.2, 1 or 2 U/mL Multifect PR 6L or Cibenza DP100, or 0.02, 0.1 or 0.2 U/mL of Ronozyme ProAct for 16 hours.

Figure 1B:
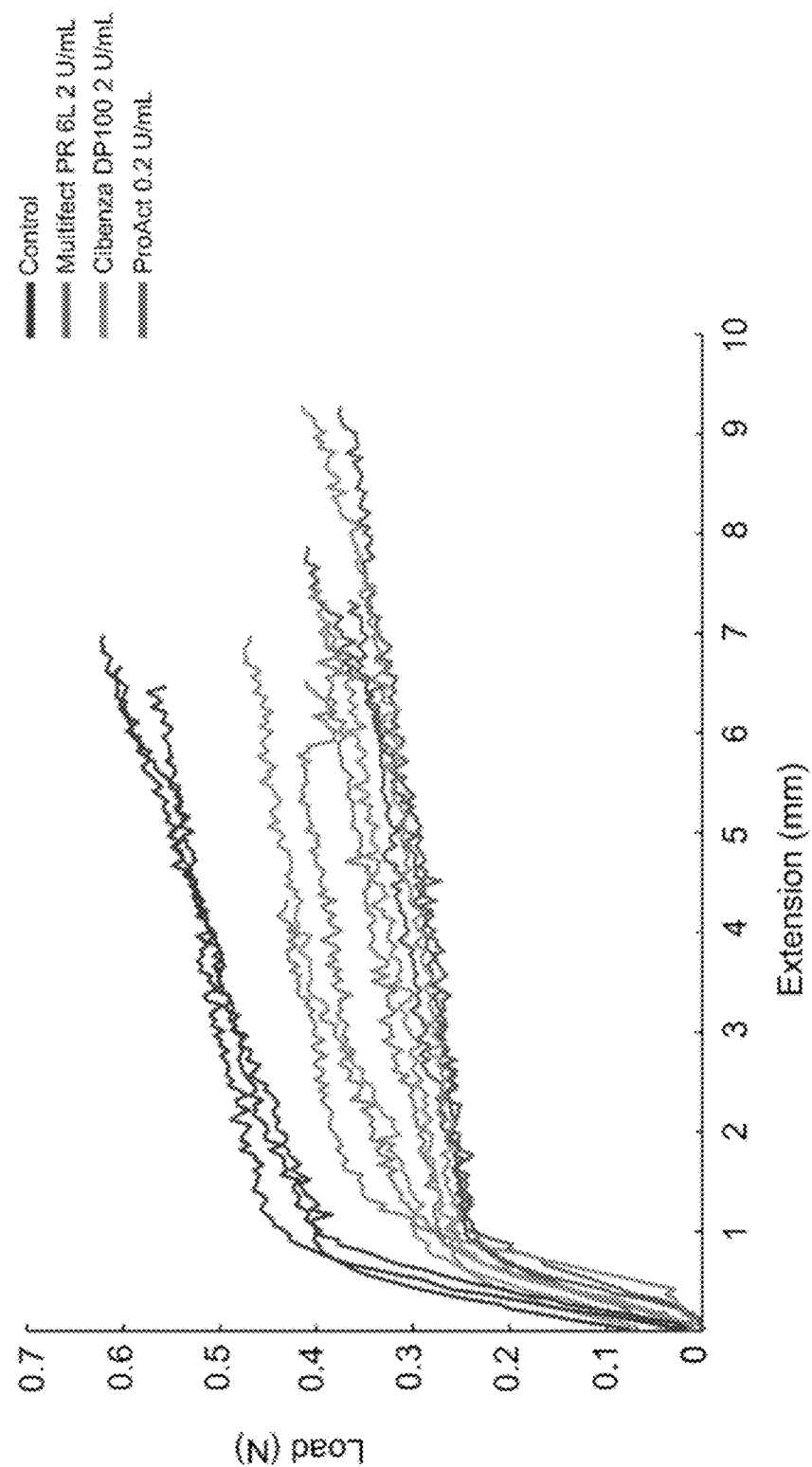

Hair samples were clamped on MTS Microforce Tryton 250 force meter and axial force testing conducted at room temperature. Samples treated with 1 or 2 U/mL Multifect PR 6L or Cibenza DP100 showed decreased force to break, while treatment with 0.2 U/mL of enzyme did not show any effect when compared to the control sample (FIGS. 1A and 1B). Ronozyme ProAct had greater effect on the hair fibres than the other enzymes, a concentration as low as 0.1 U/mL showed a marked decrease in hair force to break (FIG. 1A).

FIG. 1B shows load-extension curves for control and enzymatically treated hair. A typical load-extension curve of a hair fibre shows three regions. A first linear section, the Hookean region, where the hair behaves mostly elastically, a transformation region where the α-helix coils uncoil and may transform into β-sheets, and a post-transformation region where the remaining α-helices and/or β-sheets are stretched until the hair reaches the breaking point (Kreplak 2001). Curves in FIG. 1B do not show an obvious turnover point between the transformation and post-transformation regions. This is due to the low strain rate used in this study and might be consequence of a continuous α-β transformation before rupture commonly observed at low strain rates (Yu 2017 Structure and mechanical behaviour of human hair).

It appears that the hair samples treated with Cibenza DP 100, Multifect PR 6L or Ronozyme ProAct have decreased resistance to stretch. This is revealed by the altered Hookean region of the load-extension curves of the enzymatically treated hair compared to the control samples. According to Feughelman et al, this section corresponds to the resistance of α-helices to stretching, usually provided by the hydrogen bonds between the turns of the helices (Feughelman 1982). As a result, the enzymatically treated hair has less resistance to stress (load) and shows a decreased force to break (FIGS. 1A and B).

Enzymatic Degradation of Hair and Effect of Reducing Agents

Hair samples from cattle hides were treated for 16 hours with Cibenza DP100 and Ronozyme ProAct with the addition of different concentrations of reducing agents (i.e. sodium sulfite or sodium thioglycolate). Hair degradation studies were not continued with Multifect PR 6L since this enzyme showed low keratinase activity when compared to Cibenza DP100 and Ronozyme ProAct (Table 2).

The keratinolytic activity of Cibenza DP100 and Ronozyme ProAct in the presence of reducing agents was determined by the keratin azure assay (Table 3). Both enzymes showed increased activity in the presence of reducing agents. From the concentrations tested, 1% of sodium sulfite and 2% sodium thioglycolate showed the best improvement of activity in each case.

TABLE 3

Keratinase activity in presence of reducing agents as determined by keratin azure assay.

| Enzyme | Reducing agent | pH | Specific Activity ($10^3$ U/g of protein) |
|---|---|---|---|
| Cibenza DP100 | No reducing agent | 8 | 16 ± 1 |
| | 1% Sodium sulfite | 8 | 18 ± 1 |
| | 2% Sodium sulfite | 8 | 18 ± 1 |
| | 1% Sodium thioglycolate | 8 | 22 ± 2 |
| | 2% Sodium thioglycolate | 8 | 23 ± 2 |
| | 5% Sodium thioglycolate | 8 | 22 ± 2 |
| Ronozyme ProAct | No reducing agent | 10 | 262 ± 5 |
| | 1% Sodium sulfite | 10 | 338 ± 2 |
| | 2% Sodium sulfite | 10 | 235 ± 3 |
| | 1% Sodium thioglycolate | 10 | 470 ± 14 |
| | 2% Sodium thioglycolate | 10 | 684 ± 60 |
| | 5% Sodium thioglycolate | 10 | 391 ± 18 |

One unit of enzyme activity is defined as the amount of enzyme causing an increase of 0.1 in absorbance at 440 nm after incubation for 30 min at 37° C.

Figure 2A:
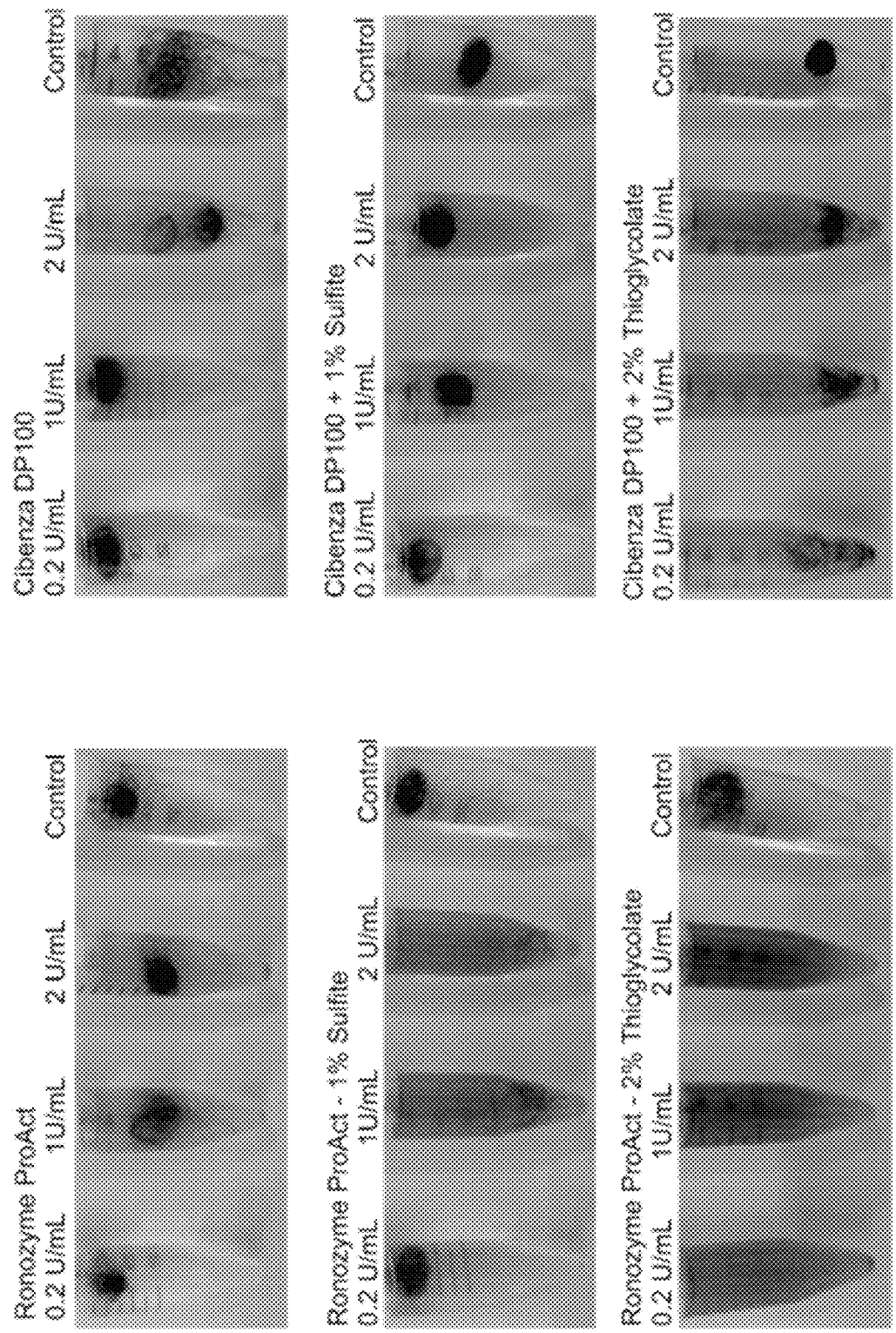
FIGS. 2A and 2B.
Figure 2B:
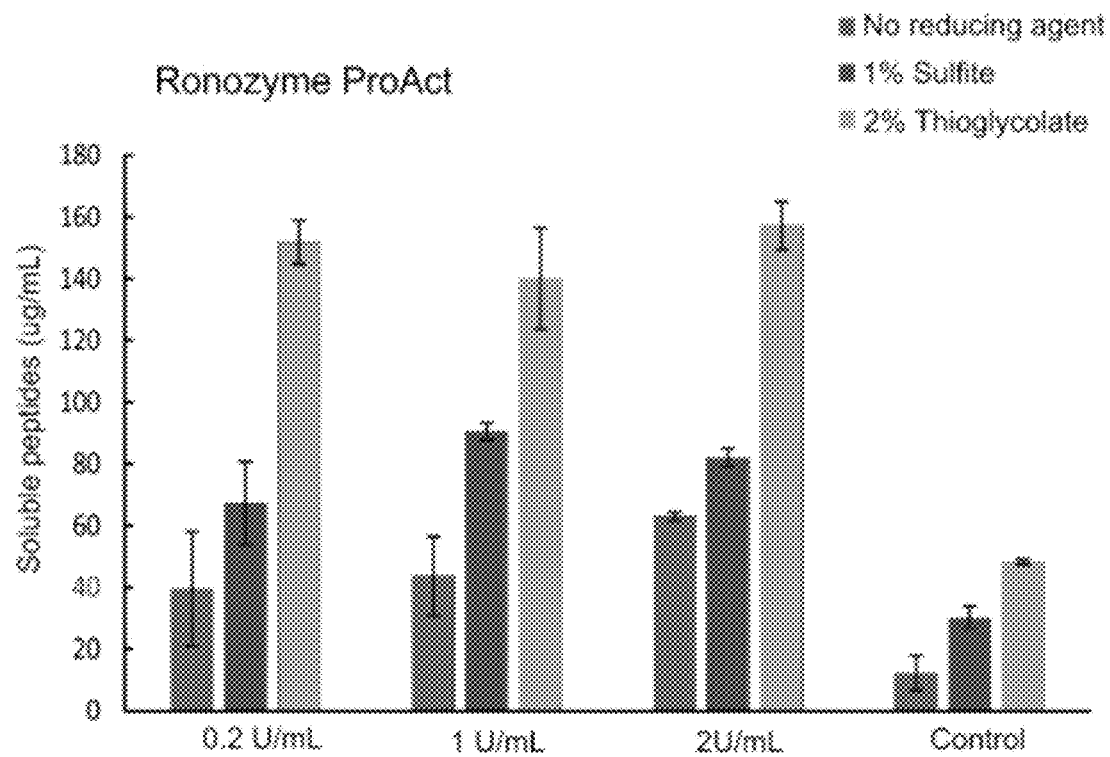
Figure 2B:
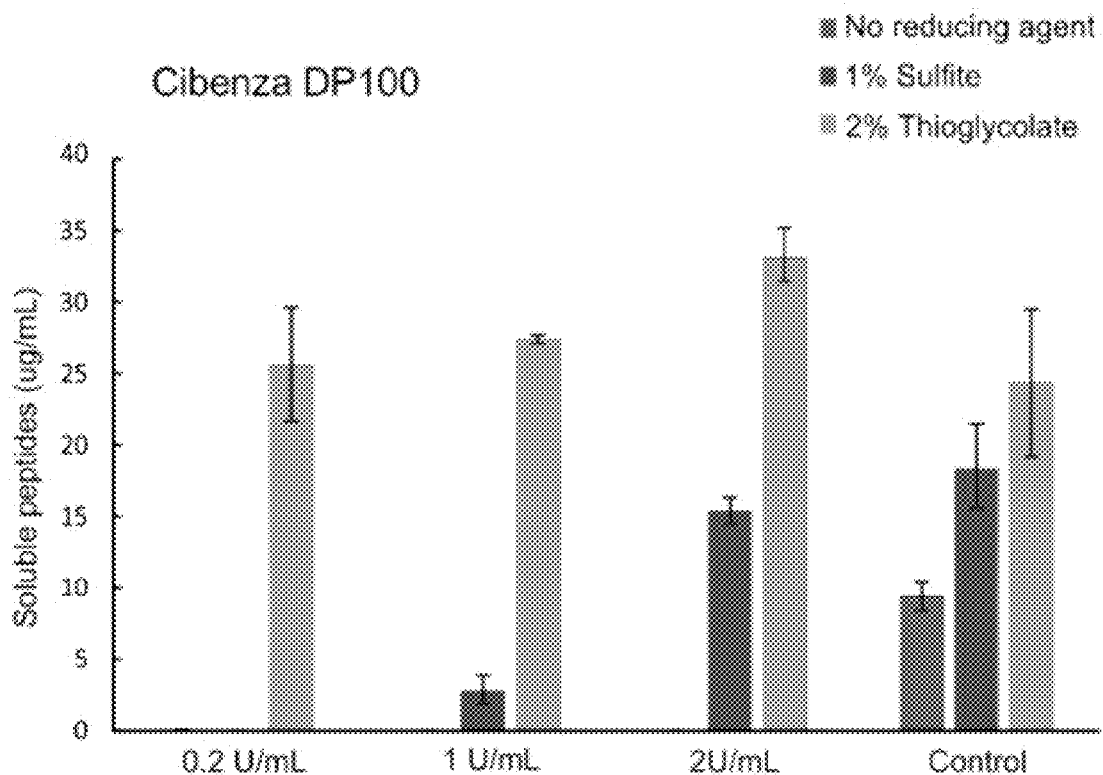

The extent of hair degradation after enzymatic treatment in the presence of reducing agents was quantitatively studied by the measurement of released soluble peptides using the Bradford assay (FIG. 2). Hairs were treated with 0.2, 1 or 2 U/mL of Cibenza DP100 or Ronozyme ProAct with or without 1% of sodium sulfite or 2% sodium thioglycolate at 37° C. The degree of degradation of hairs into soluble peptides was markedly higher for Ronozyme ProAct than for Cibenza DP100 under the same conditions and the same loading of enzyme units (FIG. 2). The presence of reducing agent had strong effect on hair degradation, which was observed by an increase in the concentration of soluble peptides in the no-enzyme control treated samples. The addition of reducing agents improved the effect of Cibenza DP100 and Ronozyme ProAct on hair degradation. In fact, Cibenza DP100 did not show detectable levels of soluble peptides unless reducing agent was added to the reaction. From the two reducing agents tested, 2% sodium thioglycolate had a greater effect on the activity of both enzymes (FIG. 2).

Scanning Electron Microscopy Studies of Enzymatic Hair Degradation

Figure 3A:
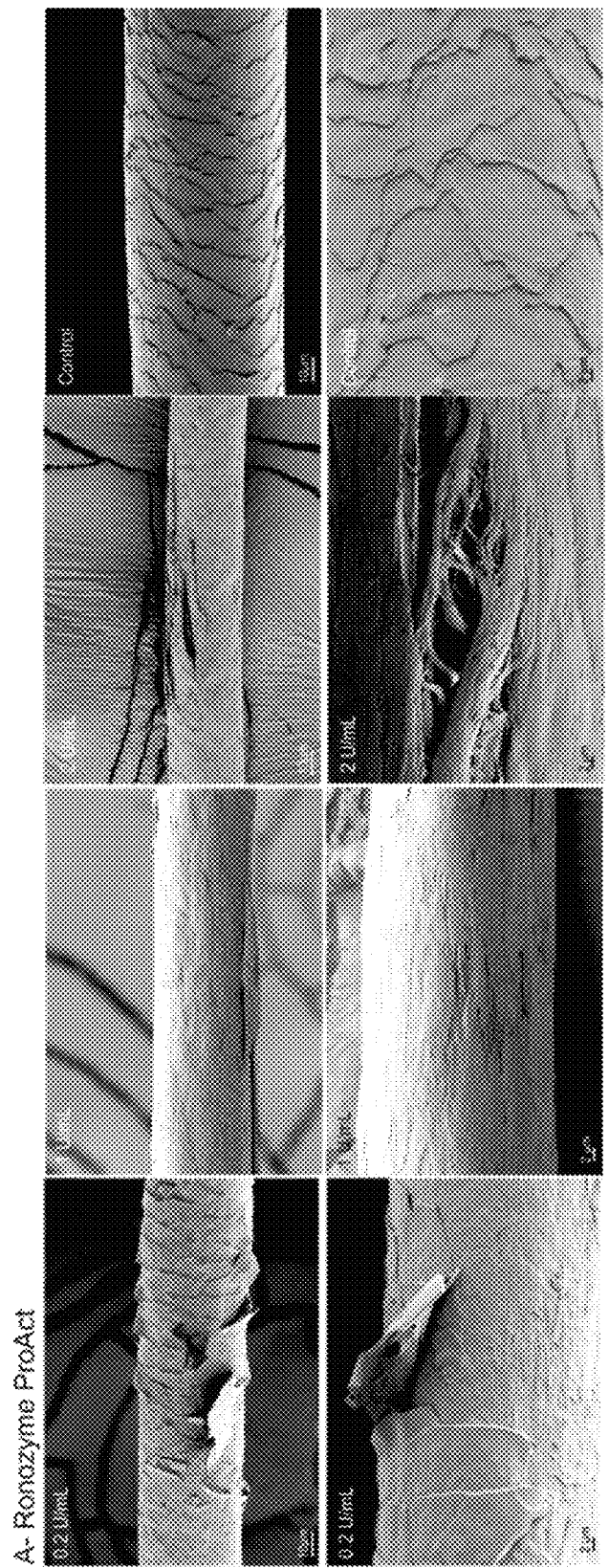
FIGS. 3A-3C: Hair treated for 16 h with 0.2 U/mL, 1 U/mL or 2 U/mL of Ronozyme ProAct, without reducing agent (FIG. 3A), with 1% sodium sulfite (FIG. 3B) or with 2% sodium thioglycolate (FIG. 3C). Control samples treated without enzyme, with or without reducing agents. Two different images and magnifications (higher magnification on the bottom row) are shown for each treatment.

Following on these results, hair samples were treated with 0.2, 1 or 2 U/mL of Cibenza DP100 or Ronozyme ProAct with or without reducing agent for 16 hours at 37° C. and analysed by SEM. FIGS. 3 and 4 show representative SEM images obtained after each treatment. As expected, the increase in concentration from 0.2 to 2 U/mL of enzyme increased damage to the hair fibre (FIGS. 3 and 4). While 0.2 U/mL of Ronozyme ProAct showed lifting of the cuticle of the hair, 1 U/mL of this enzyme completely removed the cuticle and affected the cortex (FIG. 3A). Furthermore, treatment with 2 U/mL of Ronozyme ProAct showed regions with extensive fractures to the hair fibres (FIG. 3A). Treatment with Cibenza DP 100 also showed increased damage with increasing concentration of enzyme, however the extent of degradation of the hair fibre was reduced when compared to Ronozyme ProAct (FIG. 4A). The cuticle was completely removed with 2 U/mL of Cibenza DP100 and initial damage to the cortex was observed. FIG. 3A shows control hair samples incubated in buffer with no addition of enzymes or reducing agents. In these samples, the cuticle cell surface exhibits entire cuticles, in a good general condition.

Figure 3B:
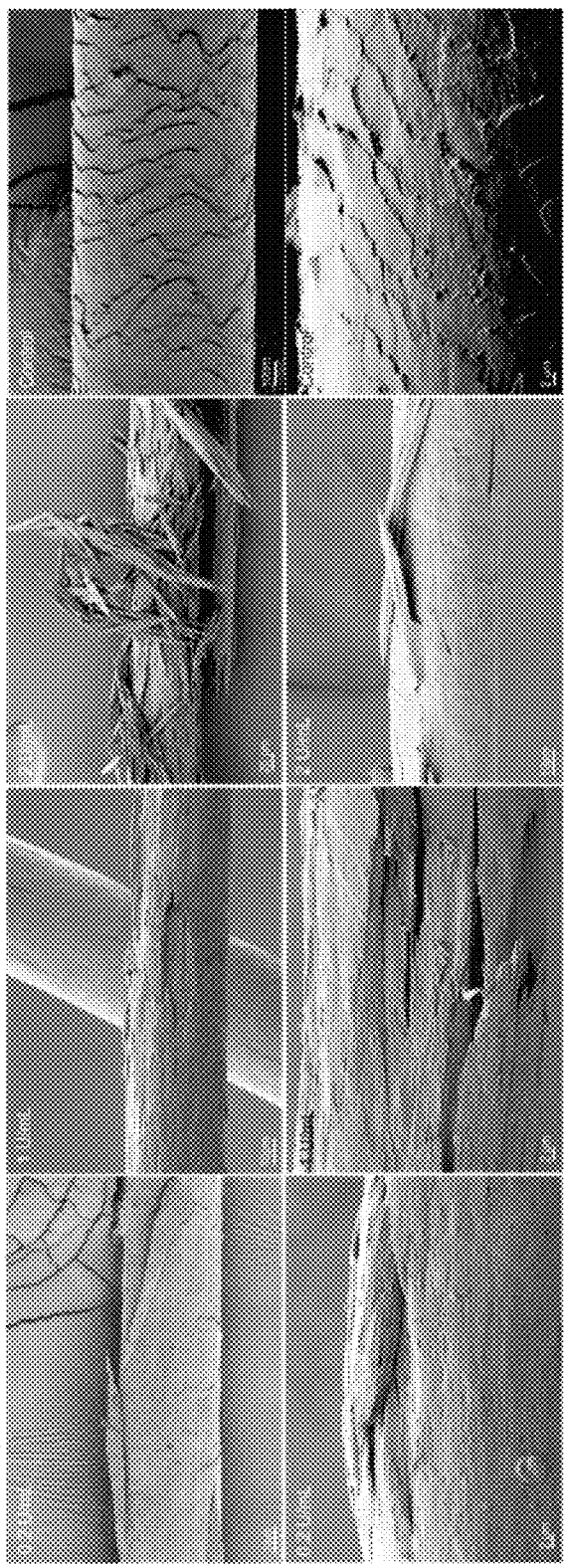
Figure 3C:
Figure 4A:
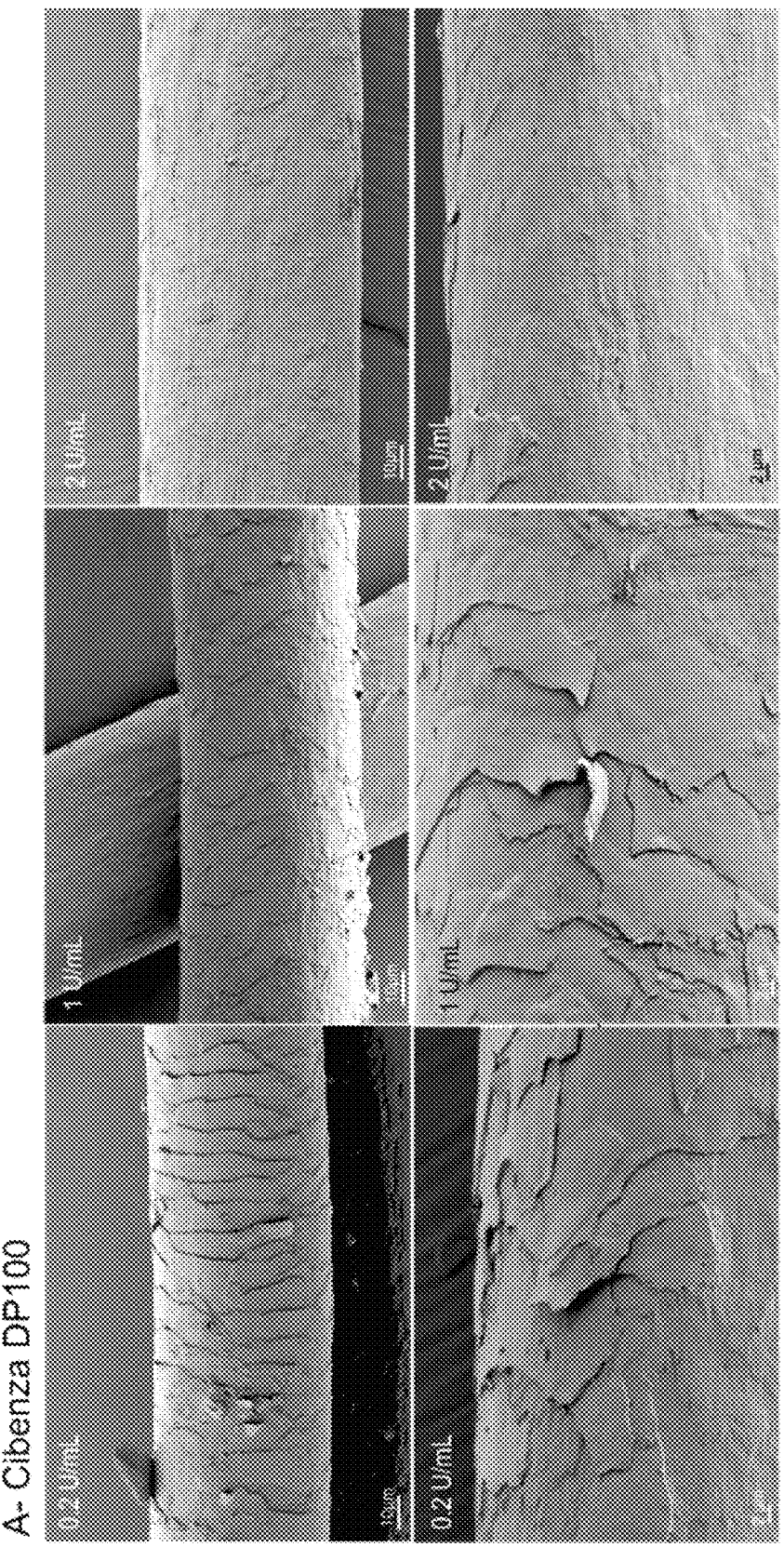
FIGS. 4A-4C: Hair treated for 16 h with 0.2 U/mL, 1 U/mL or 2 U/mL of Cibenza DP100 without reducing agent (FIG. 4A), with 1% sodium sulfite (FIG. 4B) or with 2% sodium thioglycolate (FIG. 4C). Two different images and magnifications (higher magnification on the bottom row) are shown for each treatment.
Figure 4B:
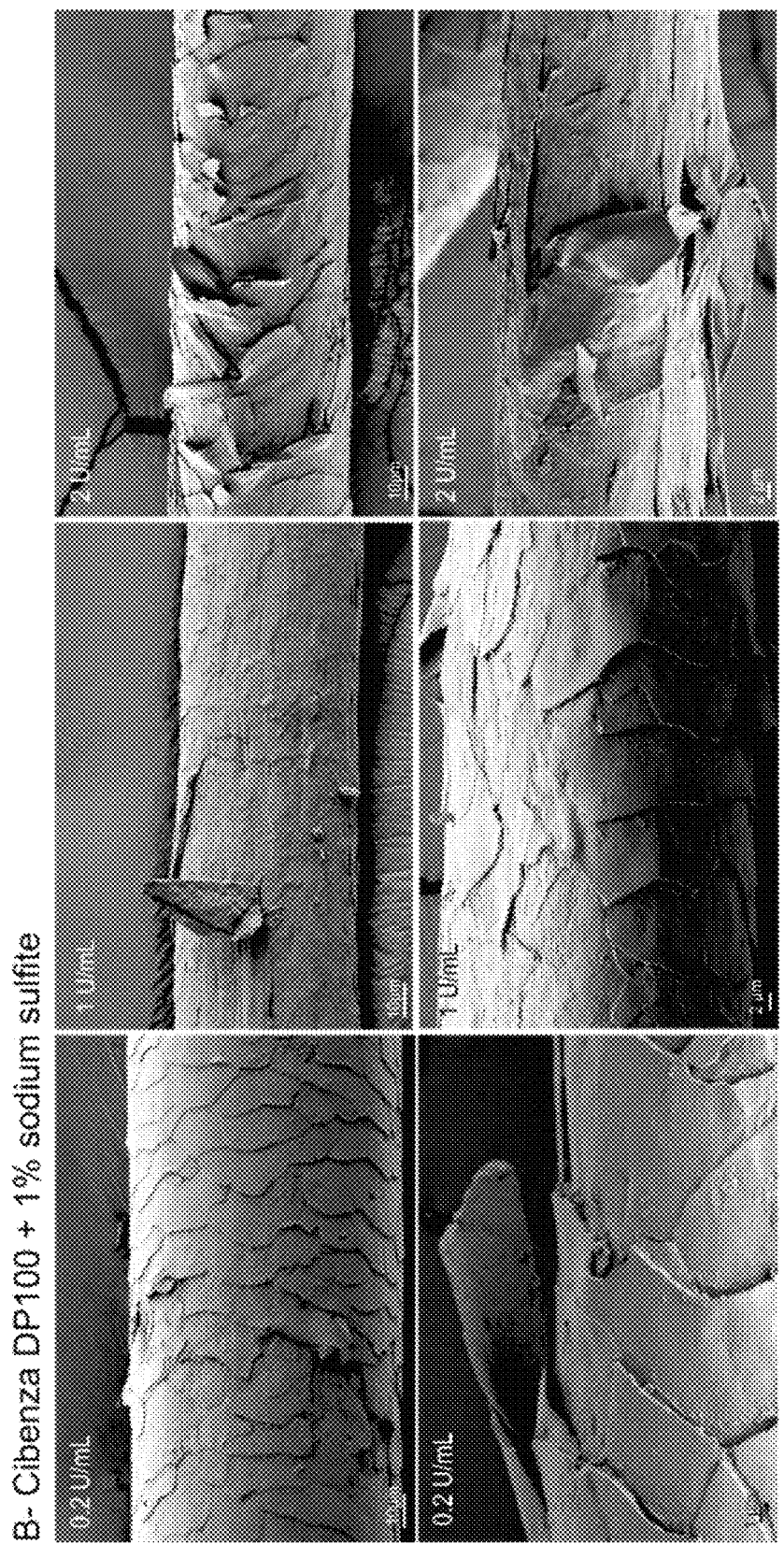

The addition of reducing agents to enzymatic treatments had a clear effect on hair degradation for both enzymes tested (FIGS. 3B and C, 4B and C). The presence of 1% sodium sulfite in hair treatments with 0.2 U/mL Ronozyme ProAct showed a complete removal of the cuticle surface and initial damage to the cortex (FIG. 3 B). Extensive fracturing of the hair fibre was observed with 1 U/mL or 2 U/mL of Ronozyme ProAct under this condition (FIG. 3B). The addition of 1% sodium sulfite to enzymatic treatments with Cibenza DP 100 enhanced hair degradation; extensive removal of the hair cuticle was observed with 1 U/mL, while hair fractures could be detected with 2 U/mL of enzyme (FIG. 4B). Control samples treated with sodium sulfite without enzyme showed minor lifting of the cuticle surface in same areas (FIG. 3B).

Figure 4C:
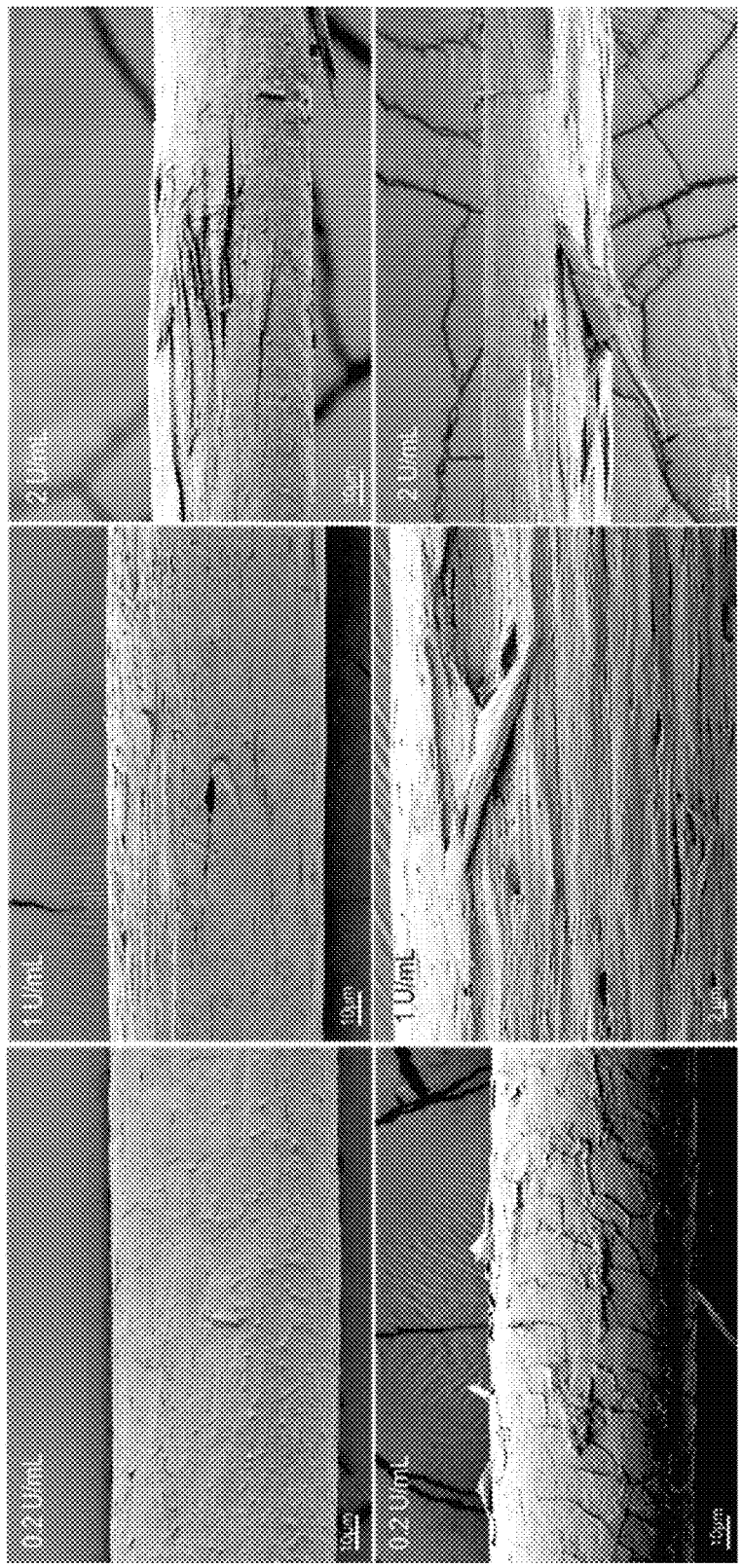

Enzymatic hair treatments conducted in the presence of 2% sodium thioglycolate revealed an extended hair structure degradation. This effect was more obvious for Ronozyme ProAct than Cibenza DP 100 (FIGS. 3C and 4C). 0.2, 1 or 2 U/mL of Ronozyme ProAct completely degraded the hair fibre in presence of 2% sodium thioglycolate (FIG. 3C). The fracturing was very significant, only small fragments of hair could be observed during SEM imaging. Similarly to the results obtained with sodium sulfite, treatment with Cibenza DP 100 in presence of 2% sodium thioglycolate improved keratinase activity of this enzyme (FIG. 4C). Hair fracturing was evidenced with 2 U/mL of enzyme under this reducing condition, however, the damage to the hair fibre was reduced when compared with Ronozyme ProAct treated samples. The presence of sodium thioglycolate in non-enzymatically treated samples showed some lifting of the hair cuticle (FIG. 3C).

Time Point Studies of the Enzymatic Degradation of Keratin

Figure 5A:
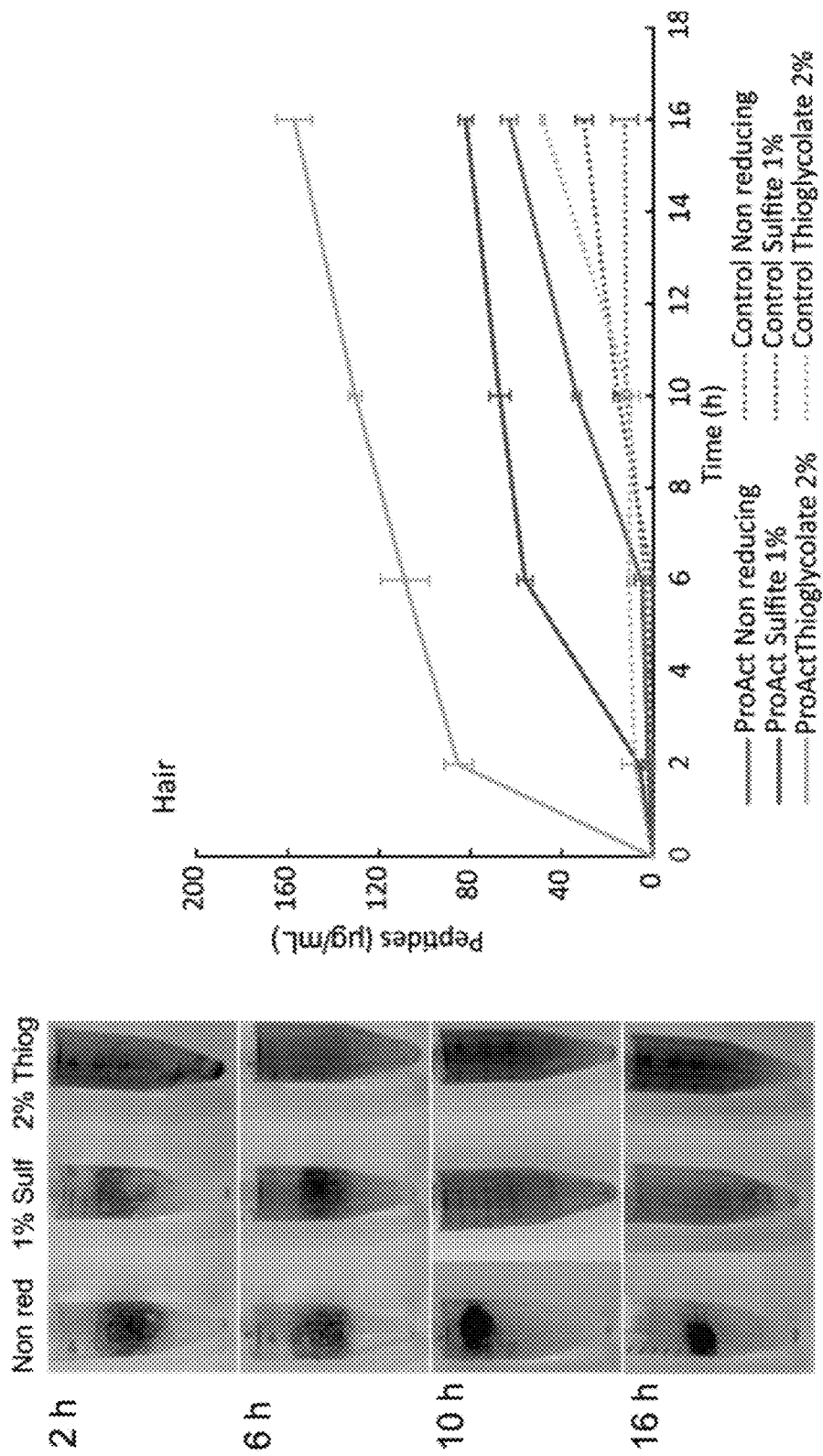
FIGS. 5A and 5B: Soluble peptides (µg/mL) after hair (FIG. 5A) and feather (FIG. 5B) treatment with 2 U/mL of Ronozyme ProAct with or without reducing agents at 37° C. The control is defined as hair or feather sample treated in buffer solution without enzyme and with or without reducing agents. Error bars correspond to standard deviation from biological duplicates. Non red corresponds to Non-reducing, 1% Sulf corresponds to 1% Sulfite and 2% Thiog corresponds to 2% thioglycolate in the figure above.
Figure 5B:
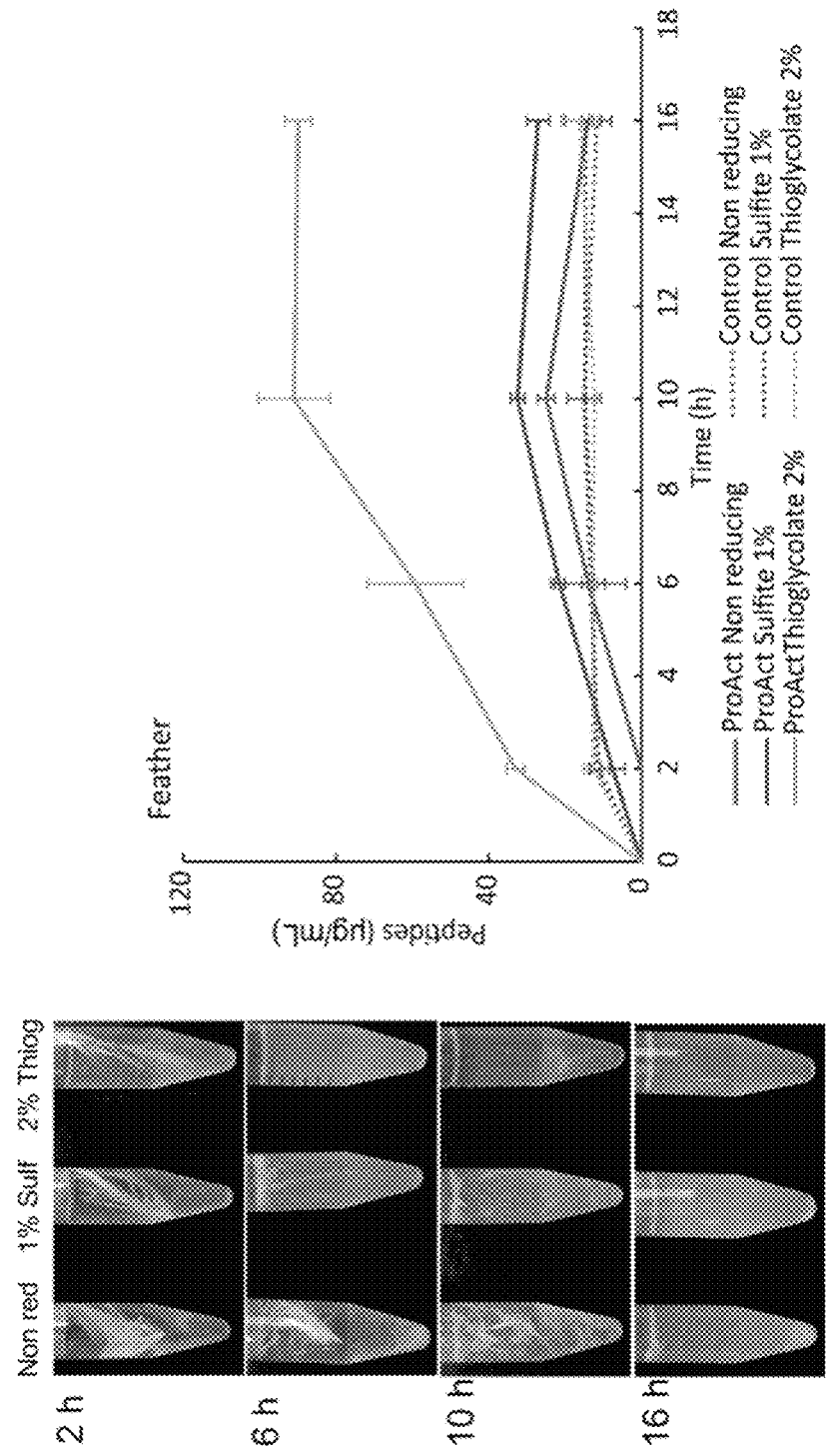

Hair and feathers were used as keratin substrates for these studies. Samples were treated with 2 U/mL of Ronozyme ProAct with or without reducing agents and soluble peptide concentration was quantified using the Bradford assay at different time points (2, 6, 10 and 16 hours) (FIG. 5). Since Ronozyme ProAct showed better keratinolytic activity compared to Cibenza DP100, these studies were performed with this enzyme only.

The degree of degradation of hair and feathers was clearly enhanced by the addition of reducing agent. The presence of 2% thioglycolate decreased the time for enzymatic degradation, most extensive decomposition occurred during the first two hours of treatment under this condition. Furthermore, both hair and feather samples were extensively degraded after 6 hours treatment, as observed in the photographs in FIG. 5. The same effect, although not as marked, was observed for 1% sulfite.

Figure 6A:
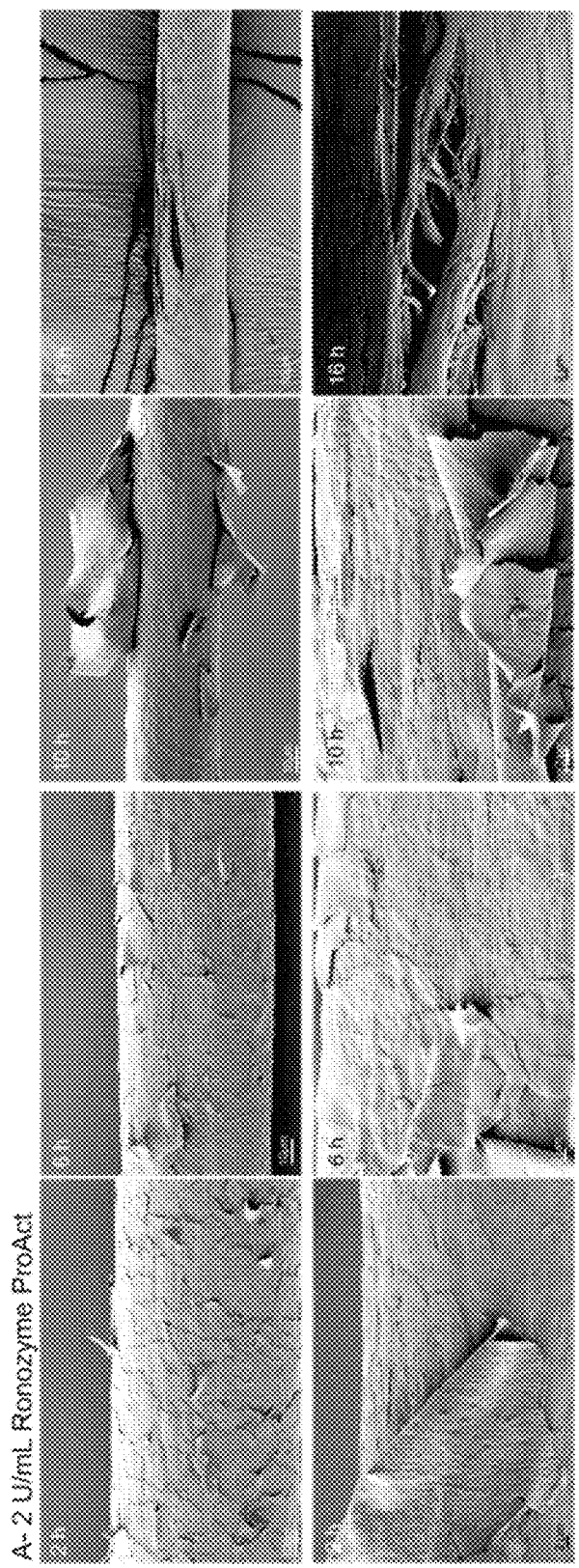
FIGS. 6A-6C: Hair treated with 2 U/mL Ronozyme ProAct without reducing agent (FIG. 6A), with 1% sodium sulfite (FIG. 6B) or with 2% sodium thioglycolate (FIG. 6C) for 2, 6, 10 and 16 hours at 37° C. Two different images and magnifications (higher magnification in the lower row) are shown for each time and treatment.
Figure 6B:
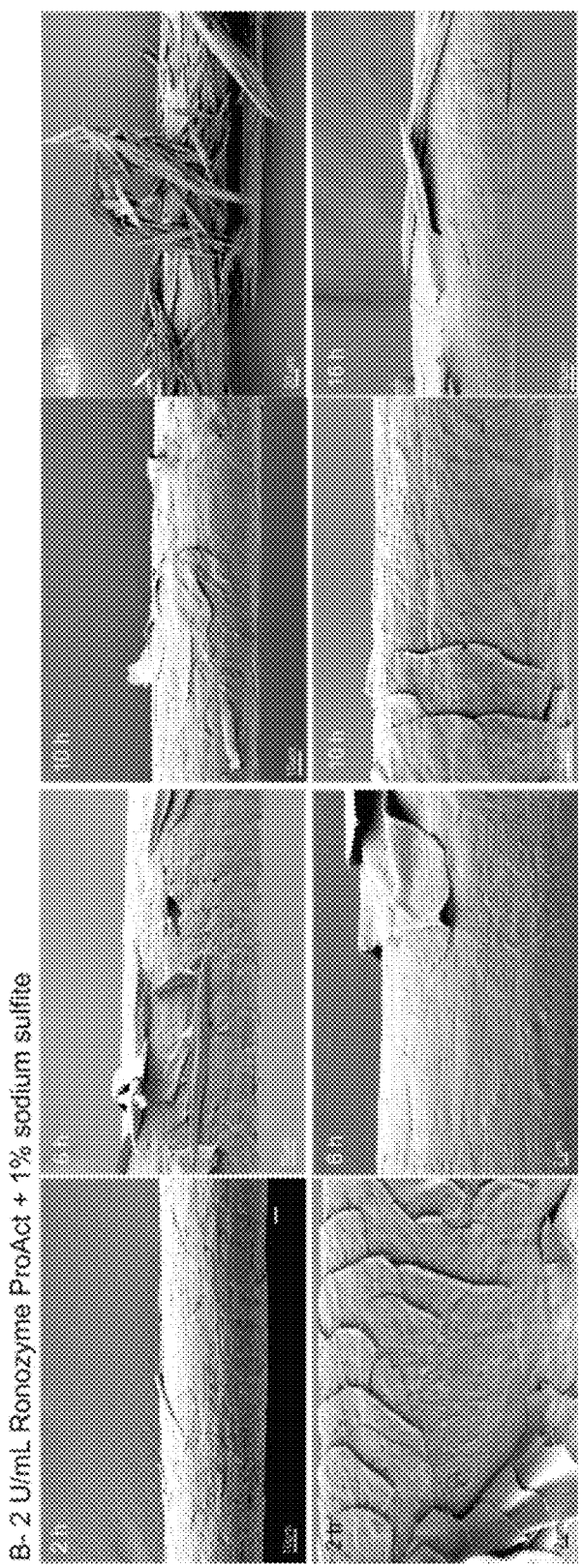
Figure 6C:
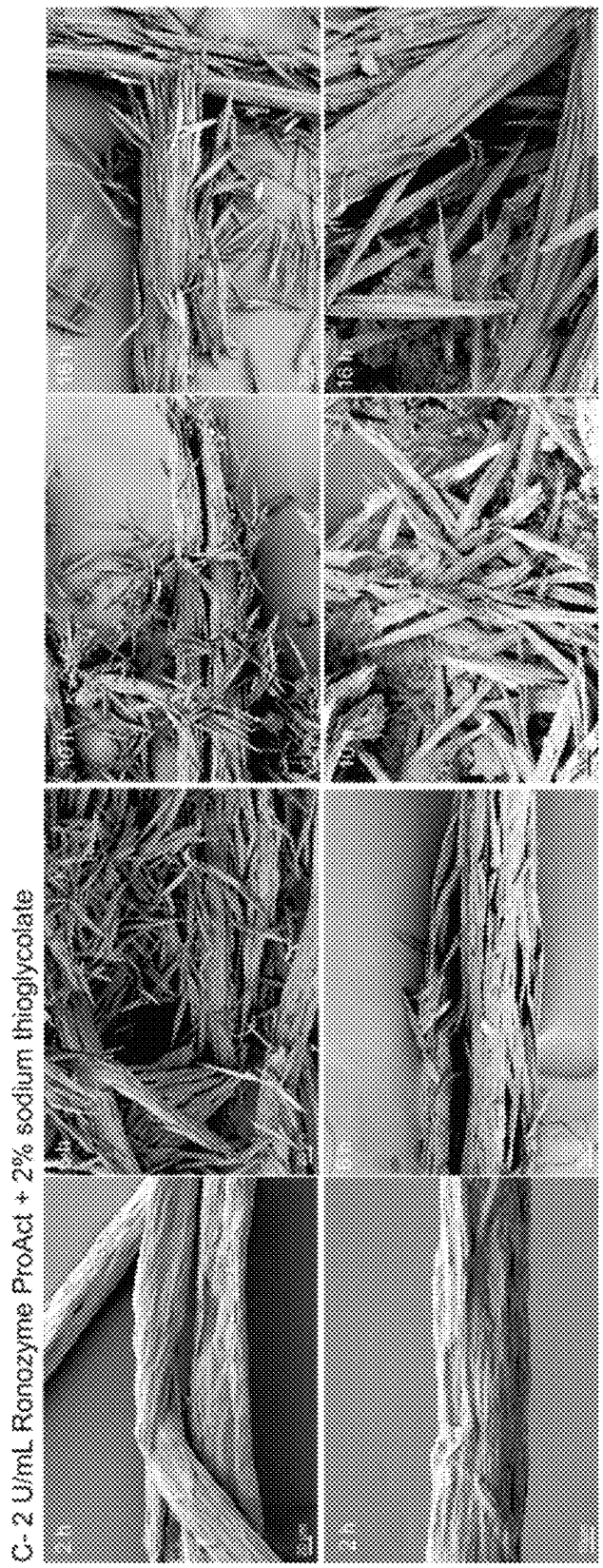

Following these results, SEM was performed to investigate the different stages of enzymatic keratin decomposition. Samples from the different time points of treatment (2, 6, 10 and 16 hours) were analysed by secondary electron imagining (FIGS. 6 and 7). Well-defined stages of hair and feather decomposition were identified. In the case of hair, the first stage of degradation was lifting of the cuticle until complete depletion. This process occurred from 0 to 16 hours of treatment with 2 U/mL of Ronozyme ProAct without reducing agent. From 6 hours onwards, the cortex of the hair appeared affected, with small fracturing detectable, followed by more extensive hair fibre fracturing at around 16 hours of treatment (FIG. 6A). The addition of reducing agent facilitated the degradation process, as previously observed in the measurements of soluble peptides in solution (FIG. 6A). For 1% sodium sulfite, variability in the degree of degradation was observed for samples taken at 6 and 10 hours of treatment with Ronozyme ProAct. Some samples suffered cortex fracturing as soon as 6 hours while other hairs retained part of the cuticle until 10 hours of treatment (FIG. 6B). Complete depletion of the cuticle layer was observed at 16 hours of treatment under this condition, with extensive fracturing of the hair fibre compared with enzymatic treatment without reducing agent (FIG. 6A). Small fragments of hair looking like splintered wood where observed at this time point. Interestingly, 2 hours of keratinase treatment in the presence of 2% sodium thioglycolate showed great weakening of the fibre and no cuticle remaining. Samples looked like splintered debris after 6 hours of treatment under this condition (FIG. 6C). SEM images of control samples after 16 hours of treatment in buffer solution with or without reducing agents are shown in (FIG. 3).

Figure 7A:
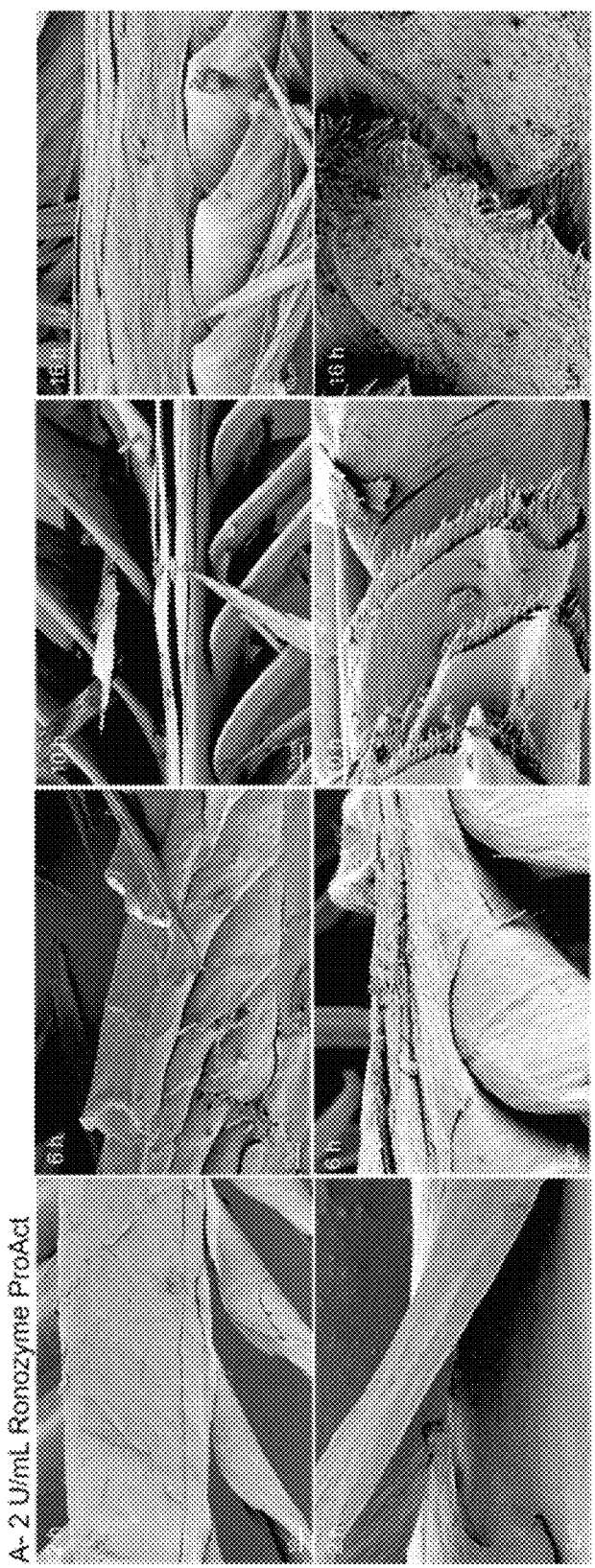
Figure 7B:
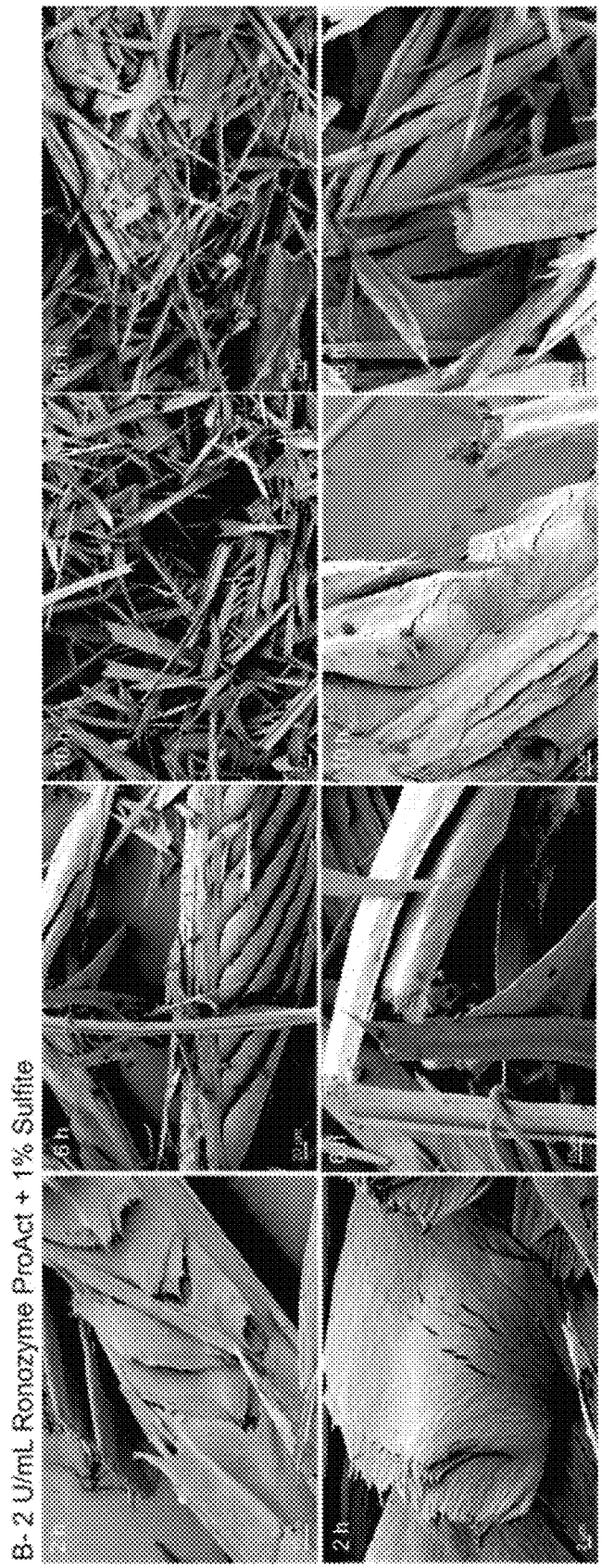

Keratin degradation from feathers also revealed well-defined stages of decomposition (FIG. 7). After 2 hours treatment with 2 U/mL of Ronozyme ProAct some fractures were revealed on barbs, however, extensive fracturing and complete breaking of barbules was observed from 6 hours of treatment onwards (FIG. 7A). After 16 hours, the structure of the feather was transformed in a material with porous appearance. The addition of reducing agents to the treatment decrease the time required for the enzymatic degradation process (FIGS. 7B and C), as observed for hair samples. Marked fracturing of barbs and barbules were observed after 2 hours treatment with Ronozyme ProAct in the presence of 1% sodium sulfite and a great extent of decomposition after 6 hours of treatment (FIG. 7B). The addition of 2% sodium thioglycolate to the enzymatic treatment had a strong effect on feather structure, after 2 hours incubation feathers were degraded into porous keratin material (FIG. 7C). At 6 hours of treatment, feathers were transformed into sheets of porous keratin and from 10 hours onwards the structure was completely degraded to an amorphous protein material (FIG. 7C).

Discussion

In this Example, we studied the degradation of hair and feather keratin by enzymes. We tested several commercial proteases for keratinolytic activity and the ones that showed activity towards keratin, Cibenza DP100, Multifect PR 6L and Ronozyme ProAct, were used for decomposition studies.

Hair mechanical properties studies were conducted to investigate the weakening of the hair fibre after enzymatic treatment. The analysis of load vs extension curves showed that treatment with the three enzymes, Cibenza DP100, Multifect PR 6L or Ronozyme ProAct decreased the hair force to break. Ronozyme ProAct showed to be the most efficient keratinase, requiring lower enzyme load to decrease hair stress to break. The weakening of the hair fibre causing premature rupture could be related to the loss of cuticle and the weakening of the hair cortex. Robbins and Crawford published the first experimental evidence that the cortex and not the cuticle is responsible for the tensile properties of hair by showing that severe damage to the cuticle only cannot be detected by tensile property evaluation (Robbins and Crawford 1991). In fact, we observed loss of cuticle and affected cortex during SEM imaging of hair enzymatically treated under the same conditions.

We also investigated the incorporation of reducing agents in the enzymatic treatments. Keratin is very recalcitrant due to its high degree of disulfide bonds. Initial attack of the disulfide bonds by reducing agents facilitates proteolytic activity by enzymes. We tested two well-known reducing agents, sodium sulfite and sodium thioglycolate. Both compounds markedly improved enzymatic degradation of keratin, however, sodium thioglycolate showed better results than sodium sulfite. This was evidenced during soluble peptide quantification, where the addition of reducing agents to the enzymatic treatments increased the concentration of peptides in solution; and also during SEM imaging, where the addition of reducing agents revealed extensive decomposition of hair and feathers.

From the commercial proteases with keratinase activity, Cibenza DP100, Multifect PR 6L and Ronozyme ProAct, we observed that Ronozyme ProAct was the best enzyme for keratin degradation. Multifect PR 6 L showed low activity in the keratin azure assay and only force to break experiments were conducted with this enzyme. Cibenza DP100 only showed extensive degradation of hair keratin when reducing agents were added to the treatment. Interestingly, Cibenza DP100 is *B. licheniformis* PWD-1 fermentation solubles, the bacterial producer of KerA, a subtilisin-type keratinase, and the only commercial product, from the ones tested, previously shown to have keratinase activity. Ronozyme ProAct is a serine protease from *Nocardiopsis prasina* described as a chymotrypsin-type protease. Chymotrypsin-type keratinases do not appear to be as common as subtilisin-type keratinases from *Bacillus* and *Streptomyces* species. Some keratinolytic enzymes from *Nocardiopsis* have been described, one example is NapA from *Nocardiopsis* spp. TOA-1, also a chymotrypsin-type protease (Mitsuiki 2004, Purification and some properties of a keratinolytic enzymes from an alkaliphilic *Nocardiopsis* sp). Saha et al also isolated a potent keratinolytic *Nocardiopsis* strain from poultry waste capable of completely degrading feathers but the protein sequence was not characterised (Saha 2012).

Some authors suggest that all proteases belonging to the subtilisin family could be able to degrade keratin in the presence of reducing agent or disulfide reductase, and that microorganisms that fail to grow on keratin might lack disulfide reducing potential (review Gupta 2006 Microbial keratinase and their prospective applications). Alcalase 2.4 LT, a subtilisin-type serine protease from *B. licheniformis* without keratinase activity, showed very low activity in the keratin azure assay in the presence of 1% sodium sulfite and no activity when 2% sodium thyoglycolate was added to the reaction (data not shown). According to this result, it might be possible that all subtilisin-type proteases have some activity against keratin substrates, yet, what defines a keratinase (or a superior keratinase) does not rely on the presence of reducing agents or a disulfide reductase. Undoubtedly, in presence of the same amount of reducing agent, the enzyme from *Nocardiopis prasina* (Ronozyme ProAct) was much more effective in hair and feather degradation than *B. licheniformis* PWD-1 KerA enzyme (Cibenza DP100).

Substrate specificity of keratinases has only been partially described. Most keratinases seem to prefer hydrophobic and aromatic amino acids at position P1, including KerA from *B. licheniformis* PWD-1 and NapA from *Nocardiopsis* spp. TOA-1 (Mitsuiki 2004). The enzymatic cleavage of the peptide bonds of keratin is inherently difficult because of the restricted enzyme-substrate interaction on the surface of the keratin particles. The hydrolysing ability of keratinolytic proteases may be related to their capacity to bind to compact substrates and a more exposed active site (Bockle 1995). Similar to chitinases, where C-terminal domains enable interaction with the compact and insoluble chitin substrate, a hydrophobic binding domain could be part of the keratinase amino acid sequence facilitating keratin binding (Bockle 1995, Hashimoto 2000). Bressollier and co-workers have shown that keratinase absorption to fibrous keratin occurs through electrostatic interactions (Bresolier 1999). Furthermore, the C-terminal domain of feather degrading serine protease Vpr from *B. cereus* DCUW dictates the specific substrate recognition (Ghosh 2009). The elimination of this domain in recombinant mutants of Vpr showed no ability to degrade feathers, yet maintaining activity towards casein and gelatin (Ghosh 2009). Similar substrate specificity function was demonstrated for the C-terminal domain of keratinases from *Stenotrophonomonas* spp. (Fang, Enhancement of the catalytic efficiency and thermostability of *Stenotrophonomonas* sp keratinase). Keratin absorption experiments were performed with Cibenza DP100 and Ronozyme ProAct to test the substrate binding capabilities of these enzymes. After incubation with hair, both enzymes were assayed for protease activity with the azocasein assay. Cibenza DP100 retained 72% of activity, while Ronozyme ProAct retained 51% of caseinolytic activity (data not shown). This result could be indicating better absorption ability of Ronozyme ProAct, and reflect its superior keratinase activity. Mitsuiki et al found that NAPase from *Nocardiopsis* sp. TOA-1 has a strong absorption capability towards keratin, possibly due to the presence of an efficient binding pocket for keratin (Mitsuiki et al 2004).

Some keratinases degrade certain types of keratin more easily than others, such as feathers better than wool or hair, like the keratinase from *B. pseudofirmus* FA30-1 (Kojima 2006), and vice versa, like keratinases from *Doratomyces micrsoporus* and *Paecilomyces marquandii* that hydrolyse α-keratin from skin, nail and hair but not β-keratins from chicken feathers (Friedrich and Kern 2003, Gradisar 2005). Certain properties of keratin, like fibril structure and porosity, could play a role in enzymatic hydrolysis, facilitating or impairing cleavage; however, specific substrate binding regions of keratinases might determine, in the last instance, the differential cleavage of these substrates. More crystallographic structures could help on the elucidation of different keratinase domains. Unfortunately, only the structure of Fervidolysin, the keratinase from *Fervidobacterium pennivorans*, is available.

The microscopic analysis of hair and feather samples at different time points of enzymatic treatment with and without reducing agents showed well-defined stages of keratin degradation. In the case of hair, the lifting of the hair cuticle was the first step of degradation observed, followed by its complete removal and initial damaged of the cortex. Next stage of decomposition was fracturing of the cortex that, in presence of reducing agents, was extended to the generation of small fragments of hair reassembling splintered wood pieces, and finally converted to an amorphous protein material. In the case of feathers, initial fracturing of the barbs was observed followed by extensive rupture of barbs and barbules. After this, the remaining structure of the feather was converted in a material with porous appearance and, finally, in the presence of reducing agents, into amorphous protein material.

If we think hair as twisted strands of keratin like a woven rope, then cleavage of keratin-stabilizing cysteine bonds by a reducing agent relaxes the structure facilitating keratinase access and attack to the peptides bonds. Proteolytic degradation of keratin molecules would expose more cysteine bonds that can consequently be attacked by more reducing agent. In this way, hair keratin degradation could be represented as a continuous untangling process of protein fibres until complete decomposition is obtained. A similar process would occur with feathers, a progressive unfolding of the fibril bundles of (3-keratin.

Conclusions

In this Example, we studied the decomposition of two keratin substrates, hair and feathers, by enzymes. We selected commercially available proteases with keratinolytic activity and applied them in different degradation studies. We evaluated enzymatic weakening of hair fibres by load-extension curves using three different commercial enzymes, Multifect PR 6L, Cibenza DP100 and Ronozyme ProAct. We showed that Ronozyme ProAct is the most efficient keratinase, decreasing hair force to break at much lower concentration than the other enzymes tested. Quantification of soluble peptides during enzymatic treatment of hair and feathers, confirmed that Ronozyme ProAct has the keratinase activity from the proteases tested. In fact, these experiments showed that Cibenza DP100 requires the presence of reducing agents to efficiently degrade hair. We also demonstrated that the presence of reducing agent greatly improves enzymatic keratin breakdown, particularly, sodium thioglycolate.

Lastly, we investigated the attack of hair and feathers by keratinases at different time points using SEM. The microscopic images showed well-defined stages of degradation, providing valuable insight into the process of keratin breakdown by keratinases.

EXAMPLE 2

In the present Example, we have tested commercial formulations of cellulase, xylanase, laccase and α-amylase enzymes to target the lignocellulosic components of the dags. Also investigated was the addition of surfactants to the enzymatic treatments. The addition of these substances to the enzymatic cocktail improved the decomposition results most likely by permeabilising the dag structure and facilitating the enzyme access to internal substrate. Despite this, treatment of dags with biomass degrading enzymes showed variable results.

On the other hand, attacking the interaction between the dags and the hair with keratinase showed very positive results. The treatment of dags with keratinase in the presence of a reducing agent and a surfactant facilitated the decomposition of the dag structure, presumably by degrading the hair framework and glue protein components that hold the aggregate together. When this treatment was applied to a small piece of hide, the amount of washing time to remove the dags was greatly reduced. Our results show a promising solution to the dag problem in Australian cattle and possibly in other countries, representing a reduction in water consumption as well as improvements in animal welfare.

Materials and Methods
Enzymatic Assays
Cellulase, Xylanase and α-Amylase Activity Determination The dinitrosalicylic acid reducing sugar assay (DNS assay) was performed for cellulase, xylanase and α-amylase activity determinations (Miller 1959). 40 µL of diluted enzyme in DNS assay buffer (100 mM Acetate buffer pH 5.0, 20 mM $CaCl_2$, 0.01% Tween 20) was pipetted in 200 µL wells of a 96-well PCR plate. 100 µL of enzyme substrate solution was added and sample mixed. Incubation was performed for 20 min at 37° C. After incubation, 60 µL of the DNS stop reagent was added to each sample and incubated at 100° C. for 5 min. Samples were transferred to 96 well spectrometer plate and OD measured at 530 nm. Determinations for each enzyme dilution were performed by triplicate. For blank determinations, 100 µL of substrate was added after addition of DNS stop reagent and treated the same way as enzyme dilution samples. Carboxymethylcellulose 1% w/v, xylan 0.4% w/v and starch 0.2% w/v were used as substrate solution for cellulase, xylanase and α-amylase activity determination, respectively. One unit of enzyme activity was defined as the amount of enzyme that releases 1 µmol of reducing sugar equivalents from the respective substrate per minute under the assay conditions used. For enzymatic activity determination under presence of surfactants, each enzyme was incubated in 50 mM acetate buffer pH 5.0 with 5% surfactant (Triton X-100, Saponin or Brij58). After 1 hour incubation at room temperature, DNS assay was performed as previously indicated. Cellulase, xylanase and α-amylase activities were determined by DNS protocol after 16 hours of dag treatment. For this, 40 µL of diluted dag treatment supernatant in 100 µL of reaction buffer was pipetted in 200 µL wells of a 96-well PCR plate and DNS protocol performed as indicated. Protein concentration was determined using Bradford assay (Bradford 1976).

Laccase Activity Determination

Enzymatic assay for laccase was performed by continuous spectrophotometric rate determination method as described by Sigma-Aldrich. Briefly, 0.5 mL of laccase was incubated with 2.2 mL of 100 mM potassium phosphate buffer pH 6.5 at 30° C. The reaction was started by addition of 0.3 mL of 0.216 mM syringaldazine and absorbance measured for 10 min at 530 nm. Blank was performed with 0.5 mL of deionized water with no addition of enzyme. One unit of enzyme activity is defined as the amount of enzyme that catalyses the conversion of 1 µmole of substrate per minute.

Enzymatic Treatment of Dags

Pieces of dag of about 5-8 $cm^3$ were incubated with individual enzymes (Spezyme LT 300, Accellerase 1500, Ronozyme Multigrain and Laccase), combination of enzymes or combination of enzymes and surfactants (Lecithin, Tween 20, Tween 80, Triton X-100, Saponin, Brij58, Genapol X-80) in 50 mM acetate buffer pH 5 in a final volume of 100 mL. Pieces of dag of about 5-8 $cm^3$ were incubated with Ronozyme ProAct with or without reducing agents (1% sodium sulfite or 2% sodium thioglycolate) and with or without 5% Triton X-100 in 100 mM Tris-Base buffer pH 10 in a final volume of 100 mL. Control experiments were performed in buffer solution with no added enzymes or surfactants. Dags were incubated for 16 hours at room temperature and decomposition was analysed by spatula testing, conferring a score according to ease of dag disruption, or by determination of total sugars in solution.

Determination of Sugar Concentration in Solution after Dag Treatment

Total sugars in solution resulting from polysaccharide degradation (e.g. cellulose, starch) before (0 hours) and after (16 hours) of dag treatment were determined using DNS protocol (Miller 1959). For this, 40 uL supernatants aliquots from each treatment were pipetted in 200 µL wells of a 96-well PCR plate. 100 µL of DNS assay buffer was added and sample mixed. Posteriorly, 60 µL of the DNS stop reagent was added to each sample and incubated at 100° C. for 5 min. Samples were transferred to 96 well spectrometer plate and OD measured at 530 nm. Determinations for each aliquot were performed by triplicate. Blanks were performed with dag treatment buffer (50 mM acetate buffer pH 5) in the presence of 5% surfactant (Triton X-100, Saponin or Brij58). Concentrations are shown as mmoles of sugar per g of dag.

Determination of Soluble Peptides

Hair samples from cow hides (Bos taurus) were treated with 2 U/mL of Ronozyme ProAct in 5 mL of 100 mM Tris-HCl buffer pH 10, for 16 hours at 22° C. or 37° C. at 200 rpm. When indicated, 1% sodium sulfite or 2% sodium thioglycolate was added. Control hair samples were incubated in reaction buffer without enzyme for 16 h at 22° C. or 37° C. at 200 rpm. Reducing agent was added when indicated. After incubation, soluble peptides were quantified using Bradford assay (Bradford 1976).

Soluble peptides in solution resulting from protein degradation after dag treatment with 10 U/mL of Ronozyme ProAct with or without reducing agents (1% sodium sulfite or 2% sodium thioglycolate) and with or without 5% Triton X-100 in 100 mM Tris-Base buffer pH 10 in a final volume of 100 mL, were assessed using Bradford assay (Bradford 1976). Control samples correspond to soluble peptides in solution after dag treatment in buffer solution with no added enzyme, with or without reducing agents or surfactants. Concentrations are shown as µg of peptide per g of dag.

Scanning Electron Microscopy

Hair samples from the inside of dag samples treated with Ronozyme ProAct for 16 hours at room temperature, with or without reducing agent (1% sodium sulfite or 2% sodium thioglycolate), were washed with water, air dried, fixed in a sample holder stub and gold coated using Leica EM SCD005 Gold Coater (~10 nm). Secondary electron images were obtained with Zeiss Σigma Field Emission Scanning Electron Microscope. Images were obtained under vacuum using 2 kV accelerating voltage.

Hide Treatment with Keratinase

A small piece of hide (15×9 cm) with dags attached was treated with 10 U/mL Ronozyme ProAct in 2% sodium thioglycolate and 5% Triton X-100 for 16 hours at room temperature with very low shaking. The treatment was performed in a container and the hide was completely covered with the enzymatic solution.

Results
Specific Activity Determination of Biomass Degradation Enzymes

Commercial enzymes for biomass (mainly lignocellulosic material) degradation were obtained from two companies, namely, Multigran Ronozyme from DSM, Accellerase 1500, Spezyme LT 300 and Laccase from Dupont (Table 4).

TABLE 4

Commercial enzymes used in the present Example

| Product Name | Enzyme type(s) | Enzyme source organism | Company |
| --- | --- | --- | --- |
| Ronozyme Multigrain | Xylanase, β-glucanase and cellulase | Information not available | DSM/Novozymes |
| Accellerase 1500 | Cellulase and β-glucosidase | Information not available | Dupont |
| Spezyme LT 300 | α-amylase | *Geobacillus stearothermophilus* | Dupont |
| Laccase | Laccase | Information not available | Dupont |
| Ronozyme ProAct | Protease/Keratinase | *Nocardiopsis prasina* | DSM/Novozymes |

Xylanase, cellulase and α-amylase specific activities were measured for Ronozyme Multigrain, Accellerase 1500 and Spezyme LT 300, respectively using the DNS protocol for reducing sugar quantification (Miller 1959). Ronozyme Multigrain was also reported by the manufacturer to have cellulase activity, therefore, it was also assayed using the DNS assay method with carboxy methyl cellulose (CMC) as the substrate. Activities are expressed as enzyme units per gram of protein as determined by Bradford assay (Table 5). The specific activity of each commercial formulation was also determined in the presence of surfactants at a concentration of 5% (weight to volume) to test the effect on enzyme activity (Table 5). Addition of Triton X-100 and Brij58 showed a statistical significant negative effect on α-amylase activity when compared to the activity with no surfactant. No statistically significant difference was observed for cellulase and xylanase activities in the presence of each surfactant.

TABLE 5

Cellulase, xylanase and α-amylase specific activities determined by DNS assay and laccase specific activity determined by the syringaldazine assay.

| Enzyme | Activity | Surfactant (5%) | Specific Activity ($10^3$ U/g of protein) |
| --- | --- | --- | --- |
| Spezyme LT 300 | α-amylase | — | 1934 ± 82 |
| | | Triton X-100 | 1608 ± 111* |
| | | Saponin | 2036 ± 79 |
| | | Brij58 | 1492 ± 81* |
| Ronozyme Multigrain | Xylanase | — | 223 ± 15 |
| | | Triton X-100 | 223 ± 6 |
| | | Saponin | 234 ± 16 |
| | | Brij58 | 229 ± 11 |
| Ronozyme Multigrain | Cellulase | — | 82 ± 8 |
| | | Triton X-100 | 77 ± 6 |
| | | Saponin | 80 ± 5 |
| | | Brij58 | 60 ± 4 |
| Accellerase 1500 | Cellulase | — | 266 ± 26 |
| | | Triton X-100 | 258 ± 12 |
| | | Saponin | 256 ± 4 |
| | | Brij58 | 281 ± 11 |

TABLE 5-continued

Cellulase, xylanase and α-amylase specific activities determined by DNS assay and laccase specific activity determined by the syringaldazine assay.

| Enzyme | Activity | Surfactant (5%) | Specific Activity ($10^3$ U/g of protein) |
| --- | --- | --- | --- |
| Laccase | Laccase | — | 627 ± 19 |
| | | Triton X-100 | 668 ± 25 |

*Statistical significant difference ($p \leq 0.01$) with no surfactant.

For the DNS assay, one unit of enzyme activity is defined as the amount of enzyme that releases 1 μmol of reducing sugar equivalents from the substrate per minute. For the laccase syringaldazine assay, one unit of enzyme activity is defined as the amount of enzyme that catalyses the conversion of 1 μmole of substrate per minute.

Enzymatic Treatment of Dags

Figure 8A:
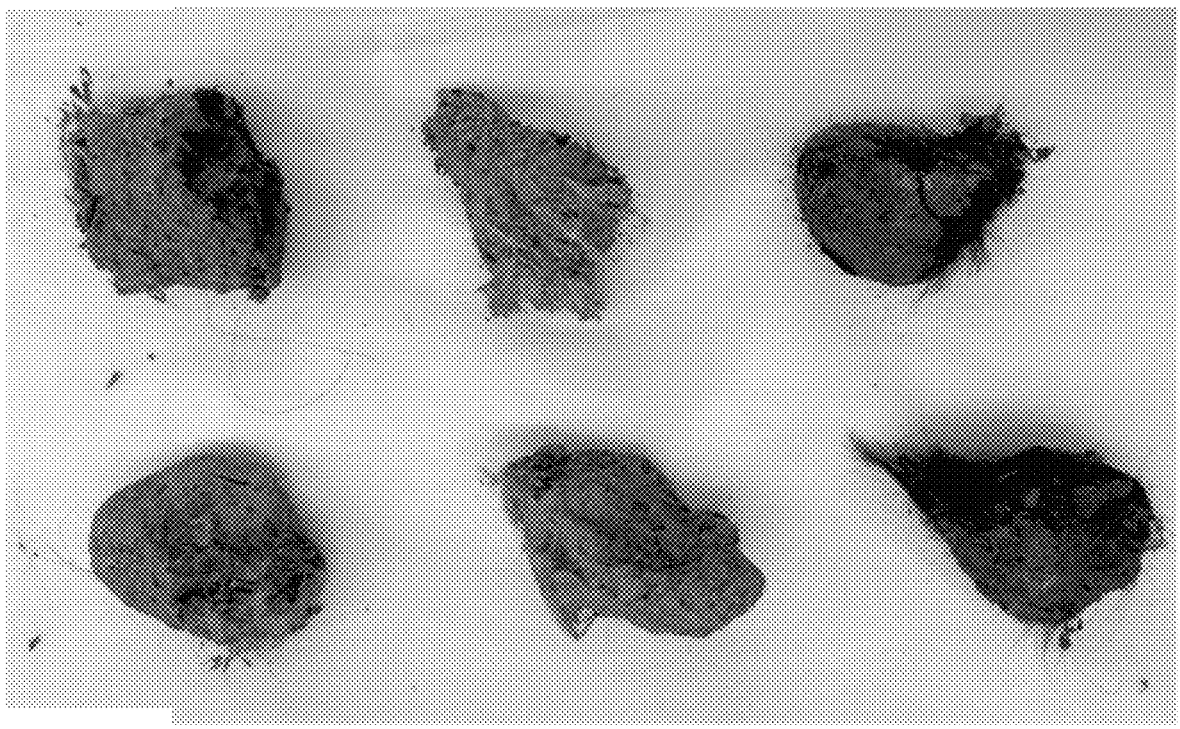
FIGS. 8A and 8B.
Figure 8B:
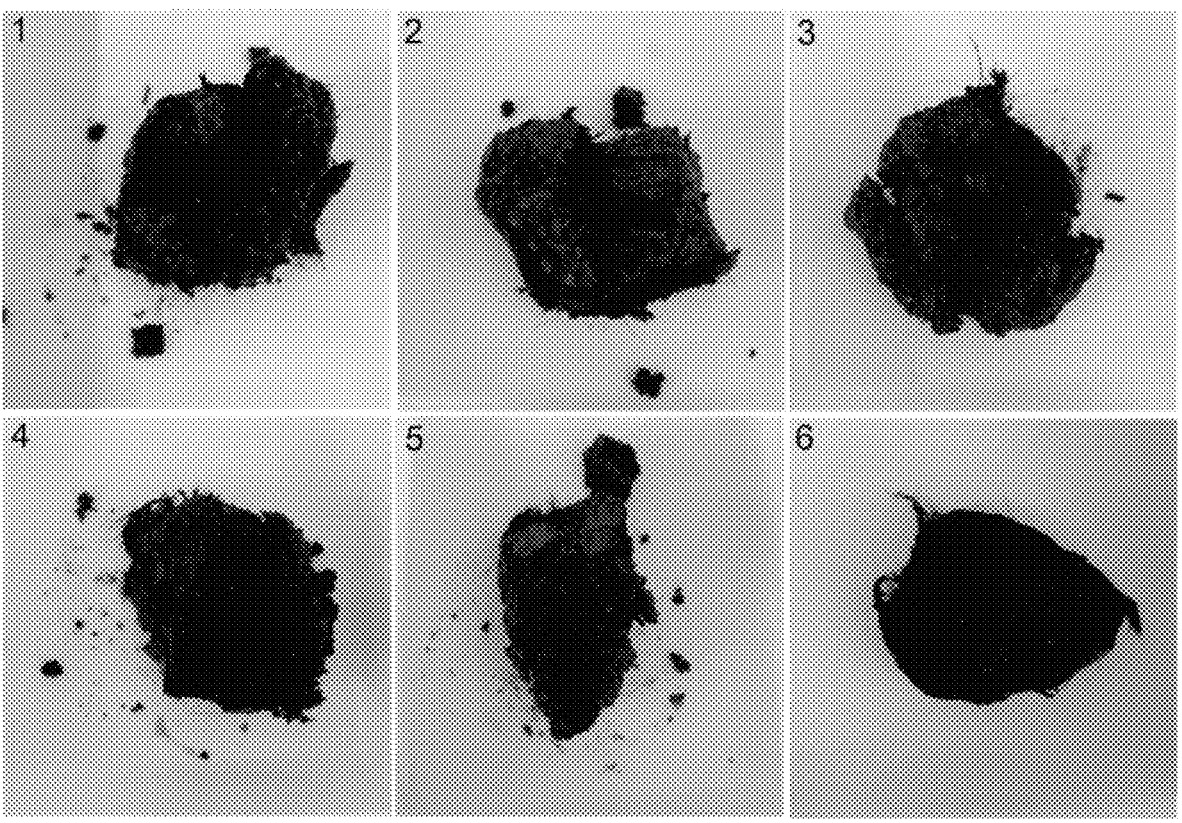

Dag samples were treated with individual or combinations of enzymes according to Table 6. The effect on dag decomposition by enzymes was initially evaluated by spatula testing, with an objective score from 1 to 6 given according to the observed ease of disruption. The addition of the individual enzymes Spezyme LT 300, Accellerase 1500 or Multigrain Ronozyme, that display α-amylase, cellulase or xylanase activities respectively, had an effect on dag decomposition when compared to the control sample. However, the combination of enzymes had a greater effect on decomposition; the best results were observed when the three enzymes Spezyme LT 300, Accellerase 1500 or Multigrain Ronozyme were used in combination in treatment 5 (FIG. 8B, Table 6). The addition of laccase to this combination did not appear to improve dag decomposition in treatment 6 (FIG. 8B, Table 6).

Following these results, dags were treated with a combination of enzymes and surfactants (Table 6). An improved degradation effect was observed when Triton X-100, Saponin or Brij58 surfactants were added to the mixture. These samples became muddier and fell apart more easily than dag samples treated with enzymes only (FIG. 8, Table 6). These results suggest the addition of surfactants could be aiding the permeabilisation of the dag structure, facilitating entry of the enzymes and contact with their substrates.

TABLE 6

Combination of enzymes and surfactants used for dag decomposition.

| | α-amylase 10 U/mL | Cellulase 10 U/mL | Xylanase 10 U/mL | Laccase 10 U/mL | Surfactant | Score |
|---|---|---|---|---|---|---|
| 1 | Spezyme LT 300 | — | — | — | — | 1 |
| 2 | — | Accellerase 1500 | — | — | — | 1 |
| 3 | — | — | Multigrain | — | — | 1 |
| 4 | — | — | — | Laccase | — | 0 |
| 5 | Spezyme LT 300 | Accellerase 1500 | — | — | — | 2 |
| 6 | Spezyme LT 300 | Accellerase 1500 | Multigrain | — | — | 3 |
| 7 | Spezyme LT 300 | Accellerase 1500 | Multigrain | Laccase | — | 3 |
| 8 | Spezyme LT 300 | Accellerase 1500 | Multigrain | — | Lecithin 0.5% | 3 |
| 9 | Spezyme LT 300 | Accellerase 1500 | Multigrain | — | Lecithin 1% | 3 |
| 10 | Spezyme LT 300 | Accellerase 1500 | Multigrain | — | Triton X-100 0.5% | 4 |
| 11 | Spezyme LT 300 | Accellerase 1500 | Multigrain | — | Triton X-100 1% | 4 |
| 12 | Spezyme LT 300 | Accellerase 1500 | Multigrain | — | Tween 20 0.5% | 3 |
| 13 | Spezyme LT 300 | Accellerase 1500 | Multigrain | — | Tween 20 1% | 3 |
| 14 | Spezyme LT 300 | Accellerase 1500 | Multigrain | — | Tween 80 2.5% | 3 |
| 15 | Spezyme LT 300 | Accellerase 1500 | Multigrain | — | Tween 80 5% | 3 |
| 16 | Spezyme LT 300 | Accellerase 1500 | Multigrain | — | Nonidet P-40 2.5% | 3 |
| 17 | Spezyme LT 300 | Accellerase 1500 | Multigrain | — | Nonidet P-40 5% | 3 |
| 18 | Spezyme LT 300 | Accellerase 1500 | Multigrain | — | Genapol X-80 2.5% | 4 |
| 19 | Spezyme LT 300 | Accellerase 1500 | Multigrain | — | Genapol X-80 5% | 3 |
| 20 | Spezyme LT 300 | Accellerase 1500 | Multigrain | — | Saponin 2.5% | 4 |
| 21 | Spezyme LT 300 | Accellerase 1500 | Multigrain | — | Saponin 5% | 5 |
| 22 | Spezyme LT 300 | Accellerase 1500 | Multigrain | — | Brij58 1% | 3 |
| 23 | Spezyme LT 300 | Accellerase 1500 | Multigrain | — | Brij58 2.5% | 4 |
| 24 | Spezyme LT 300 | Accellerase 1500 | Multigrain | — | Brij58 5% | 5 |
| 25 | Spezyme LT 300 | Accellerase 1500 | Multigrain | — | Triton X-100 2.5% | 4 |
| 26 | Spezyme LT 300 | Accellerase 1500 | Multigrain | — | Triton X-100 5% | 5 |

| | Alpha-amylase 50 U/mL | Cellulase 50 U/mL | Xylanase 50 U/mL | Laccase 10 U/mL | Surfactant | Score |
|---|---|---|---|---|---|---|
| 27 | Spezyme LT 300 | Accellerase 1500 | Multigrain | — | — | 4 |
| 28 | Spezyme LT 300 | Accellerase 1500 | Multigrain | — | Triton X-100 5% | 5 |
| 29 | Spezyme LT 300 | Accellerase 1500 | Multigrain | Laccase | — | 4 |
| 30 | Spezyme LT 300 | Accellerase 1500 | Multigrain | Laccase | Triton X-100 5% | 5 |
| 31 | — | — | — | — | — | 0 |

Figure 9:
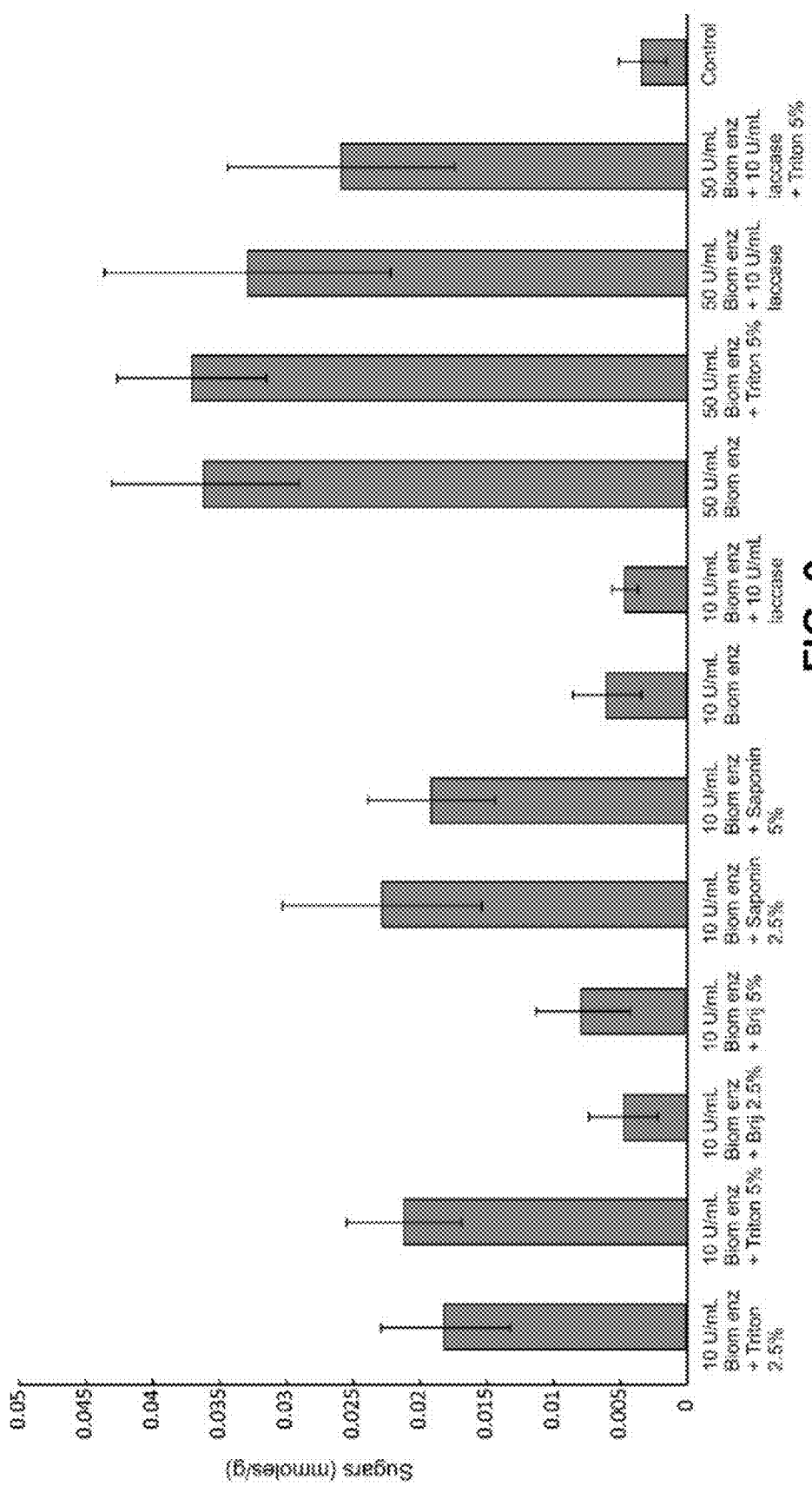
FIG. 9: Total sugars per dag weight after 16 hours of treatment. 10 U/mL or 50 U/mL of each biomass degrading enzyme, Spezyme LT 300, Accellerase 1500 and Ronozyme Multigrain (collectively termed 'Biom enz' in the above figure) were used in combination with different concentrations of surfactants for dag treatment as indicated. The control was defined as a dag sample treated with buffer solution only. Error bars correspond to standard deviation from biological triplicates.

Score
0 Does not break apart
1 Breaks apart with difficulty
2 Breaks apart with moderate difficulty
3 Breaks apart easily
4 Breaks apart very easily
5 Falls apart into pieces
6 Falls apart into pieces very easily Thirteen different treatments from the enzyme and surfactant combinations from Table 6 were analysed using the DNS protocol to test for enzymatic release of reducing sugars. Sugars in solution derived from the carbohydrate fraction of dag samples after enzyme treatment were measured as a quantitative indication of dag decomposition (FIG. 9). According to our results, the addition of Triton X-100 or Saponin to the enzyme treatment improved the release of sugars into solution. Since enzymatic activity is not enhanced in the presence of surfactants (Table 5), this effect is likely to be due to the surfactant having a physical effect on the dag, such as increasing permeability. The presence of 10 U/mL of laccase enzyme did not improve the amount of sugars obtained. When 50 U/mL of each enzyme was used for dag treatment the amount of sugars in solution increased when compared to treatment with 10 U/mL of each enzyme. The observed decomposition and the ease of disruption with spatula of the dag samples however did not show an improvement. The spatula testing score given to dags treated with 10 U/mL or 50 U/ml of each enzyme was the same in both cases (Table 6). This result implies that the degradation of the carbohydrate/lignocellulose component of the dag may not be the key pathway towards structural weakening of the dag.

During these experiments, some variability in the level of dag decomposition was observed for replicates of the same treatment, which is reflected in the scale of the error bars. This decomposition variability is likely due to the structural and compositional variability between dag samples.

Analysis of Enzymatic Activity after Dag Treatment

Xylanase (Ronozyme Multigrain), celullase (Accellerase 1500 and Ronozyme Multigrain) and α-amylase (Spezyme LT 300) activities were determined after dag treatment to test the stability of the enzymatic preparation during degradation (Table 7). Treatments with a combination of enzymes and 5% surfactant (Triton X-100, Saponin or Brij58) were selected for each activity determination.

TABLE 7

Cellulase, xylanase, α-amylase and laccase specific activities after dag treatment.

| Activity assayed | Treatment | Specific activity before treatment ($10^3$ U/g of protein) | Specific activity after treatment ($10^3$ U/g of protein) | Remaining activity after incubation time (%) |
|---|---|---|---|---|
| α-amylase | Triton X-100 5% | 1608 ± 111 | 1418 ± 70 | 88 ± 12 |
|  | Saponin 5% | 2036 ± 79 | 1526 ± 27 | 75 ± 5 |
|  | Brij58 5% | 1492 ± 81 | 1069 ± 38 | 72 ± 9 |
|  | No surfactant | 1934 ± 82 | 1324 ± 86 | 69 ± 11 |
| Xylanase | Triton X-100 5% | 223 ± 6 | 112 ± 8 | 50 ± 10 |
|  | Saponin 5% | 234 ± 16 | 105 ± 2 | 49 ± 9 |
|  | Brij58 5% | 229 ± 11 | 142 ± 12 | 62 ± 5 |
|  | No surfactant | 223 ± 15 | 131 ± 13 | 59 ± 16 |
| Cellulase | Triton X-100 5% | 335 ± 18 | 324 ± 22 | 97 ± 12 |
|  | Saponin 5% | 336 ± 9 | 381 ± 50 | 113 ± 16 |
|  | Brij58 5% | 341 ± 15 | 386 ± 21 | 113 ± 10 |
|  | No surfactant | 348 ± 34 | 392 ± 13 | 112 ± 13 |
| Laccase | Triton X-100 5% | 668 ± 25 | 547 ± 11 | 90 ± 6 |
|  | No surfactant | 627 ± 19 | 565 ± 17 | 82 ± 6 |

A decrease in α-amylase and xylanase activities is observed after 16 hours of dag treatment at room temperature (Table 7). α-Amylase and xylanase activities decreased 31% and 41%, respectively, after incubation without surfactant (Table 7). Cellulase activity did not appear to be affected under this condition. Laccase activity is not notably affected, retaining 90% of activity after dag treatment without surfactant. Furthermore, the presence of 5% surfactant (Triton X-100, Saponin or Brij58) did not have a marked effect on stability of the enzymes (Table 7).

Dag Treatment with Protease

In this project, we also investigated the use of protease enzymes to attack the interaction between the hair and the dag and also degrade the feed protein component of the dag. Protease enzymes had not previously been tested for dag degradation.

For this end, commercial protease Ronozyme ProAct was obtained DSM-Novozymes. In previous work, we had shown that this enzyme was very effective for keratin degradation and its activity can be improved in the presence of reducing agents (i.e. 1% sodium sulfite or 2% sodium thioglycolate). Table 8 shows protease and keratinase activity for Ronozyme ProAct with or without reducing agents.

TABLE 8

Keratinase activity in presence of reducing agents as determined by keratin azure assay.

| Enzyme | Reducing agent | pH | Specific Activity ($10^3$ U/g of protein) |
|---|---|---|---|
| Ronozyme ProAct | No reducing agent | 10 | 262 ± 5 |
|  | 1% Sodium sulfite | 10 | 338 ± 2 |
|  | 2% Sodium thioglycolate | 10 | 684 ± 60 |

One unit of enzyme activity is defined as the amount of enzyme causing an increase of 0.1 in absorbance at 440 nm after incubation for 30 min at 37° C.

Figure 10:
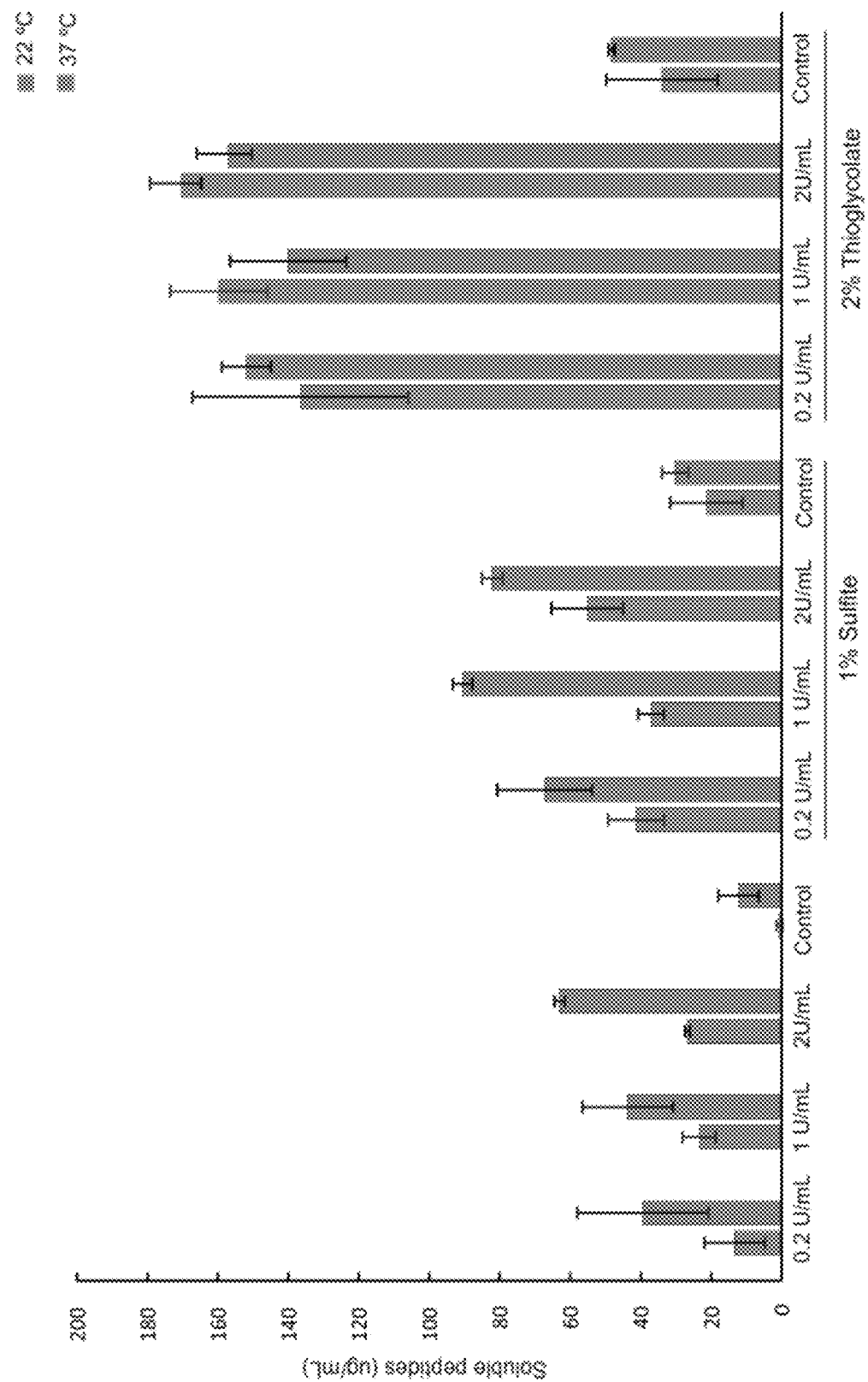
FIG. 10: Soluble peptides concentration after hair treatment with 0.2, 1 or 2 U/mL of Ronozyme ProAct in presence of reducing agents at 22° C. and 37° C.

In this work, hair samples from cow hides were treated for 16 hours with Ronozyme ProAct with or without reducing agents 1% sodium sulfite or 2% sodium thioglycolate at 22° C. and 37° C. (FIG. 10). Ronozyme ProAct has been shown to be very effective on keratin degradation at 37° C. (see Example 1), however, lower temperatures had not been previously tested. This experiment was conducted to evaluate the degradation effect of Ronozyme ProAct at lower temperatures as the enzyme would likely be applied on the farm during winter periods. The extent of hair degradation after enzymatic treatment in the presence of reducing agents was quantitatively studied by the measurement of released soluble peptides using the Bradford assay (FIG. 10). The decrease in temperature did not appear to have a strong effect when samples were treated in the presence of 2% sodium thioglycolate implying that the rate of the enzyme catalysed reaction was not limiting. However, treatment at 22° C. decreased keratin degradation compared to higher temperatures when no reducing agent was used or in the presence of 1% sodium sulfite. This decrease in activity at lower temperatures is characteristic of enzyme catalysed reactions. Each enzyme has a specific optimal temperature of activity. Moving above or below this temperature optimal will slow down the rate of catalysis in a way that is specific for each enzyme. Further experiments could be conducted at even lower temperatures that are representative of the winter seasons in different regions.

Following these results, dag samples were treated with Ronozyme ProAct with or without reducing agents according to Table 9. The effect on dag decomposition was evaluated by spatula testing, giving a score from 0 to 6 according to ease of disruption. Residual Ronozyme ProAct keratinase activity was determined after 16 hours incubation at room temperature in the presence of 5% Triton X-100 and no changes in activity were observed implying that the enzyme is highly stable in the reaction conditions.

TABLE 9

Dag treatment with keratinase.

|  | Keratinase 10 U/mL | Reducing agent | Surfactant | Score |
|---|---|---|---|---|
| 1 | Ronozyme ProAct | — | — | 5 |
| 2 | Ronozyme ProAct | 2% Thioglycolate | — | 6 |
| 3 | Ronozyme ProAct | 1% Sulfite | — | 6 |
| 4 | Ronozyme ProAct | — | Triton 5% | 5 |
| 5 | Ronozyme ProAct | 2% Thioglycolate | Triton 5% | 6 |
| 6 | Ronozyme ProAct | 1% Sulfite | Triton 5% | 6 |
| 7 | — | — | — | 0 |

Figure 11:
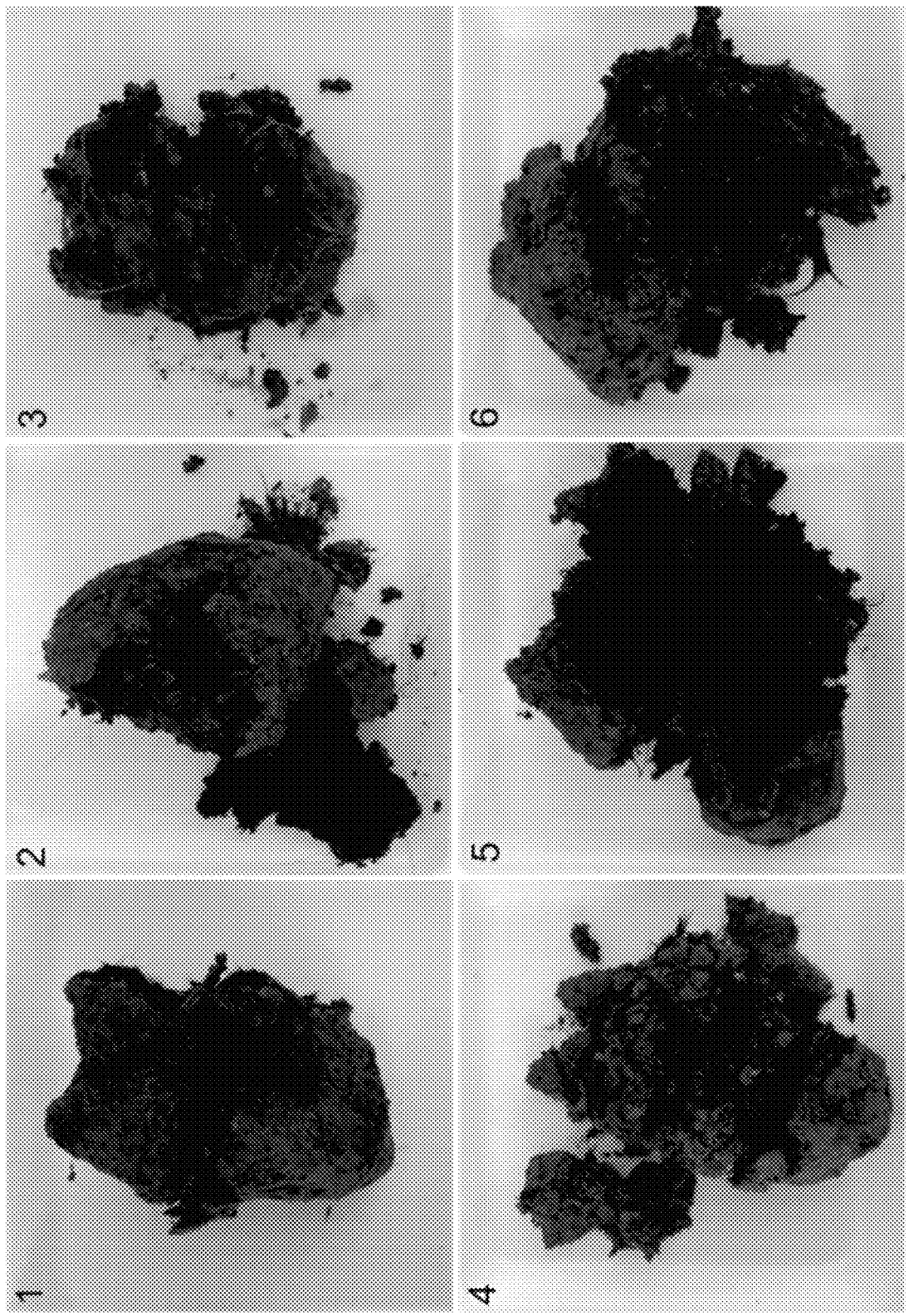
FIG. 11: Dag samples treated with 10 U/mL Ronozyme ProAct without reducing agent (1), with the addition of 2% sodium thioglycolate (2) or 1% sodium sulfite (3). Dag samples treated with 10 U/mL Ronozyme ProAct and 5% Triton X-100 without reducing agent (4), and with the addition of 2% sodium thioglycolate (5) or 1% sodium sulfite (6). Photos were taken after spatula testing.

Score
0 Does not break apart
1 Breaks apart with difficulty
2 Breaks apart with moderate difficulty
3 Breaks apart easily
4 Breaks apart very easily
5 Falls apart into pieces
6 Falls apart into pieces very easily Dag decomposition was clearly evident after treatment with Ronozyme ProAct (FIG. 11). The presence of reducing agent contributed to the degradation of the sample (FIG. 11). After 16 hours incubation, dag samples treated with keratinase and reducing agent fell easily into pieces during spatula testing. Hairs observed inside the dag appear to be loose and unattached to the biomass.

Figure 12:
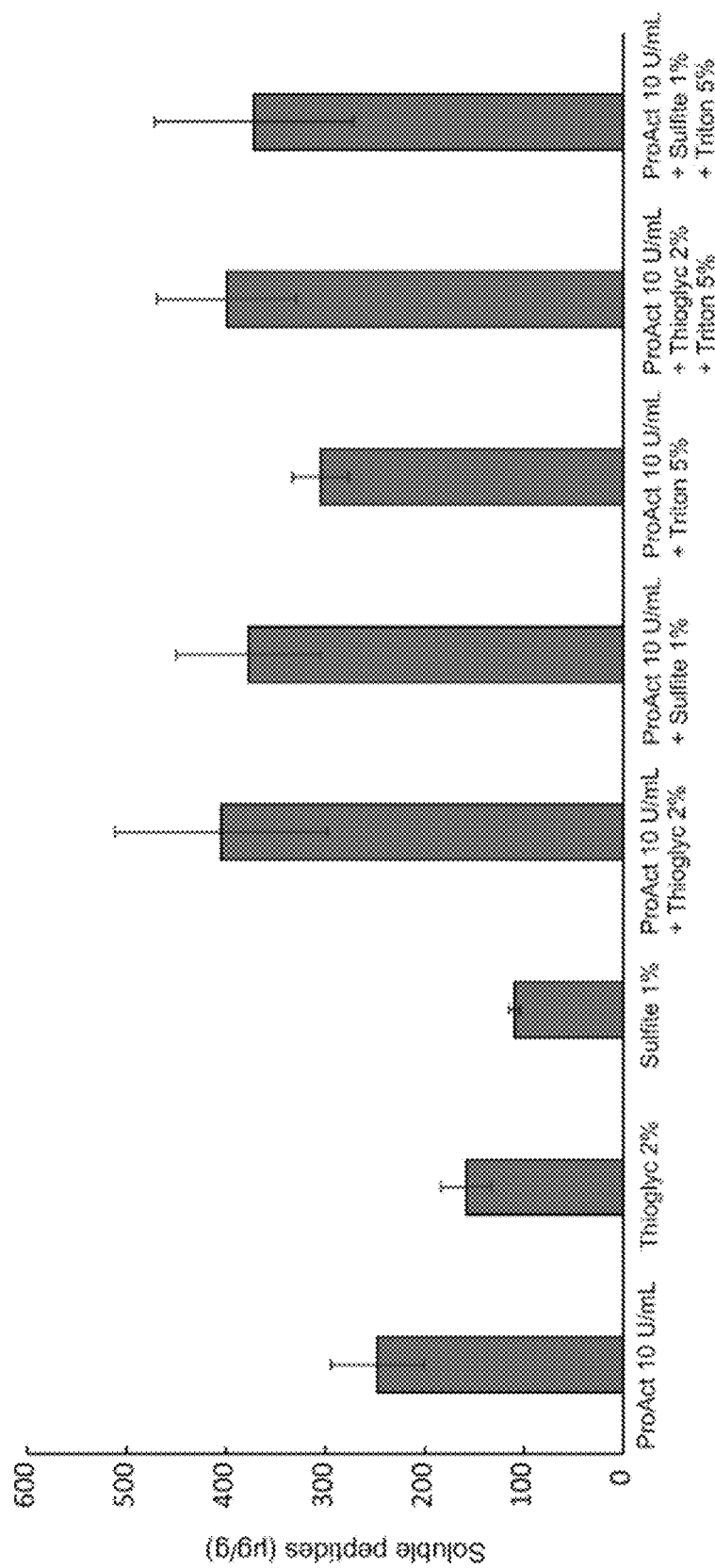
FIG. 12: Soluble peptides (µg/g) after dag treatment with 10 U/mL of Ronozyme ProAct with or without reducing agents and surfactant. Error bars correspond to standard deviation from biological duplicates. Thioglyc 2% corresponds to thioglycolate 2% in the figure above.

Soluble peptides concentration after dag treatments were measured using Bradford assay (FIG. 12). As expected from the studies performed with cattle hair (FIG. 10), where the presence of reducing agent improved keratin degradation by Ronozyme ProAct, the addition of sodium sulfite or sodium thioglycolate improved the amount of soluble peptides after dag treatment. The addition of 5% Triton X-100 did not appear to improve the release of peptides into solution. However, since the presence of surfactant improved dag decomposition when treatment was performed with biomass degrading enzymes, presumably by aiding on permeabilization of the structure, its incorporation into a keratinase dag cleaning formulation considered.

Figure 13:
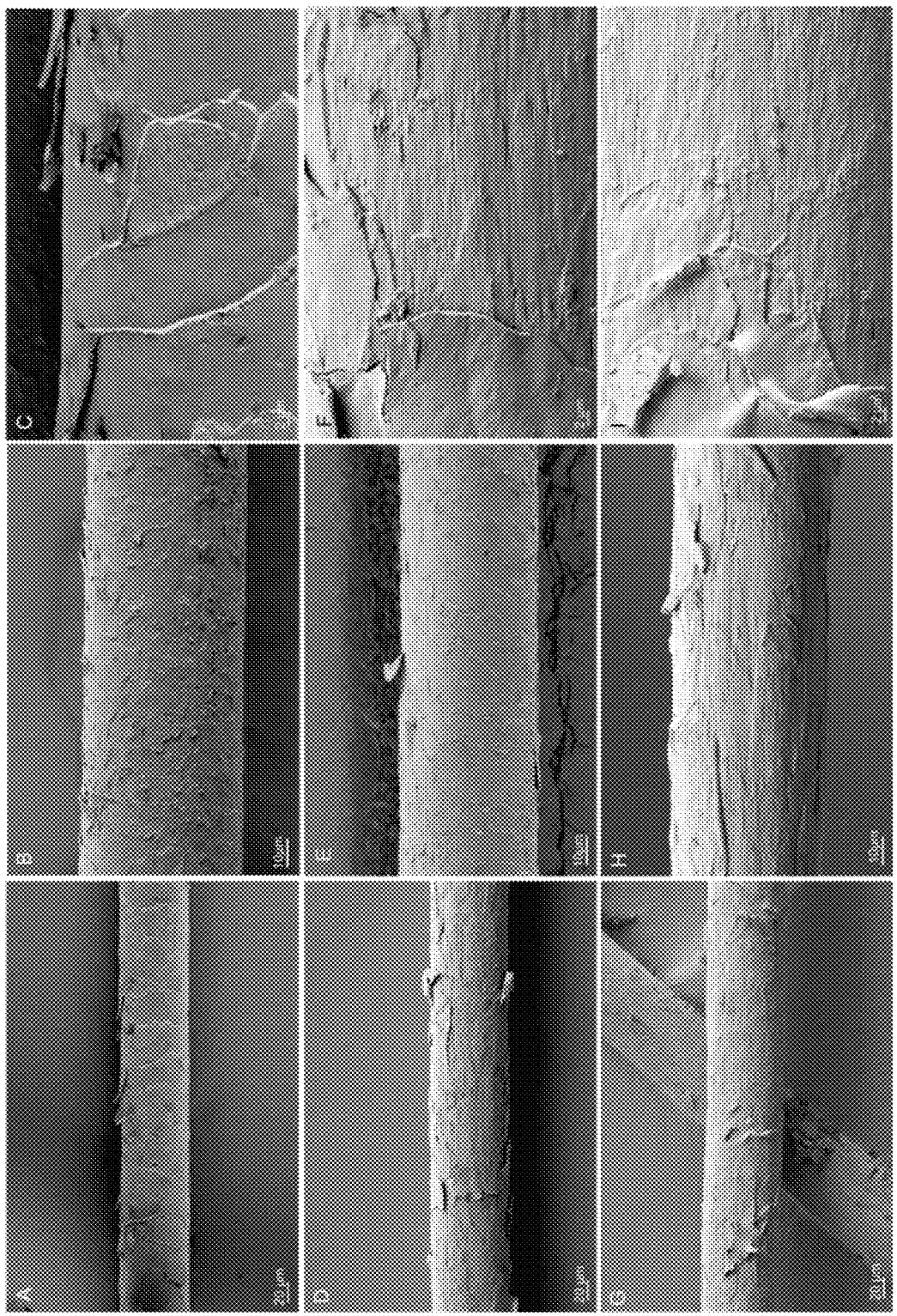
FIG. 13: Hairs from dags treated for 16 hours with 10 U/mL Ronozyme ProAct without reducing agent (A, B and C), with the addition of 1% sodium sulfite (D, E and f) or 2% sodium thioglycolate (G, H and I). Three different images on each row are increasing magnifications for each treatment.

Hairs from the dag treatments with Ronozyme ProAct with and without reducing agents were collected from inside the structure after spatula testing and studied by scanning electron microscopy (FIG. 13). Hairs from dags treated with Ronozyme ProAct without reducing agent were observed with cuticle lifting (FIGS. 13 A, B and C), while hairs from dags treated with Ronozyme ProAct in the presence of 1% sodium sulfite were observed with cuticle lifting and cortex degradation in some areas (FIGS. 13 D, E and F). Hairs from dags treated with Ronozyme ProAct in the presence of 2% sodium thioglycolate were found to have more extensive cuticle lifting and cortex degradation in all areas (FIGS. 13 G, H and I). This result clearly indicates that the enzymes are able to penetrate within the dag in active form to aid dag deconstruction. Removal of the cuticle on the surface of the hair implies that any attachment between the dag and the hair has also been removed.

Dags samples were also treated in a two-step experiment, firstly with Ronozyme ProAct for 8 hours and then with biomass degrading enzymes for 16 hours at room temperature (i.e. Spezyme LT 300, Accellerase 1500 and Multigrain Ronozyme) according to Table 8. Treatment with Ronozyme ProAct was performed at pH 10 with reducing agents. Treatment with biomass degrading enzymes was then performed at pH 5. Enzymes were not added in a single step because of the proteolytic activity of Ronozyme ProAct that may degrade the other enzymes, and the requirement of different pH for optimal activity of the enzymes.

TABLE 10

Two step dag treatment with keratinase and biomass degrading enzymes.

Step 1

| | Keratinase 10 U/mL | Reducing agent | Surfactant |
|---|---|---|---|
| 1 | Ronozyme ProAct | 2% Thioglycolate | Triton 5% |
| 2 | Ronozyme ProAct | 1% Sulfite | Triton 5% |
| 3 | — | — | — |

TABLE 10-continued

Two step dag treatment with keratinase and biomass degrading enzymes.

Step 2

| | Alpha-amylase 10 U/mL | Cellulase 10 U/mL | Xylanase 10 U/mL | | Score |
|---|---|---|---|---|---|
| 1 | Spezyme LT 300 | Accellerase 1500 | Multigrain | Triton 5% | 6 |
| 2 | Spezyme LT 300 | Accellerase 1500 | Multigrain | Triton 5% | 6 |
| 3 | Spezyme LT 300 | Accellerase 1500 | Multigrain | Triton 5% | 5 |

Figure 14:
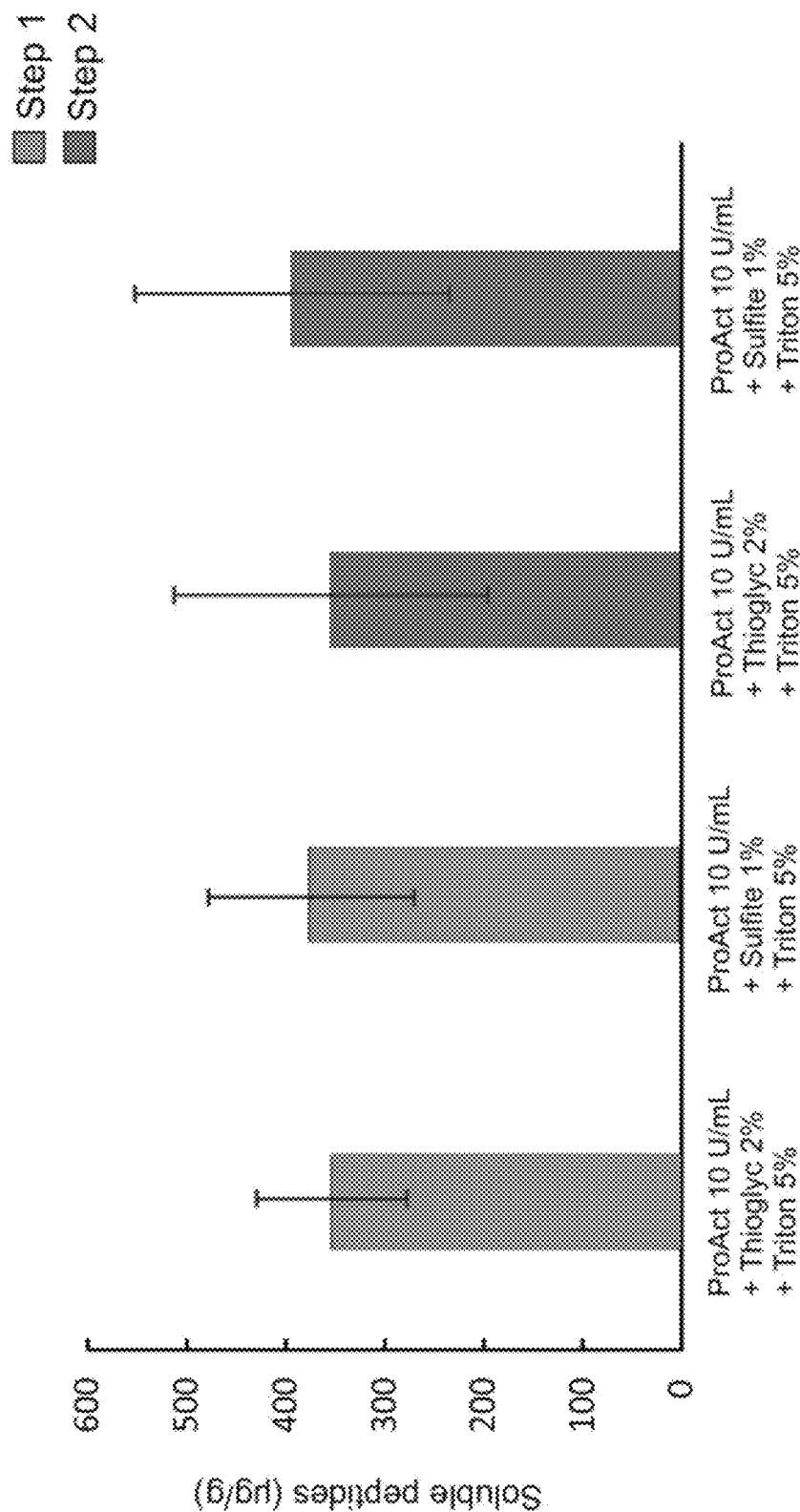
FIG. 14: Soluble peptides (µg/g) after two step dag treatment with keratinase (10 U/mL of Ronozyme ProAct) and biomass degrading enzymes (10 U/mL Spezyme LT 300, 10 U/mL Accellerase 1500 and 10 U/mL Multigrain).

Score
0 Does not break apart
1 Does not break apart easily
2 Breaks apart with difficulty
3 Breaks apart with moderate difficulty
4 Breaks apart easily
5 Breaks apart very easily
6 Breaks apart very easily into pieces The treatment with biomass degrading enzymes after keratinase treatment in presence of reducing agents did not appear to further improve the degree of dag degradation compared to the keratinase alone (Table 9 and Table 10). Soluble peptide concentration was measured after step 1 and 2, observing no further release of soluble peptides into solution after treatment with biomass degrading enzymes (FIG. 14).

Hide Treatment with Keratinase

Figures 15A, 15B, 15C:
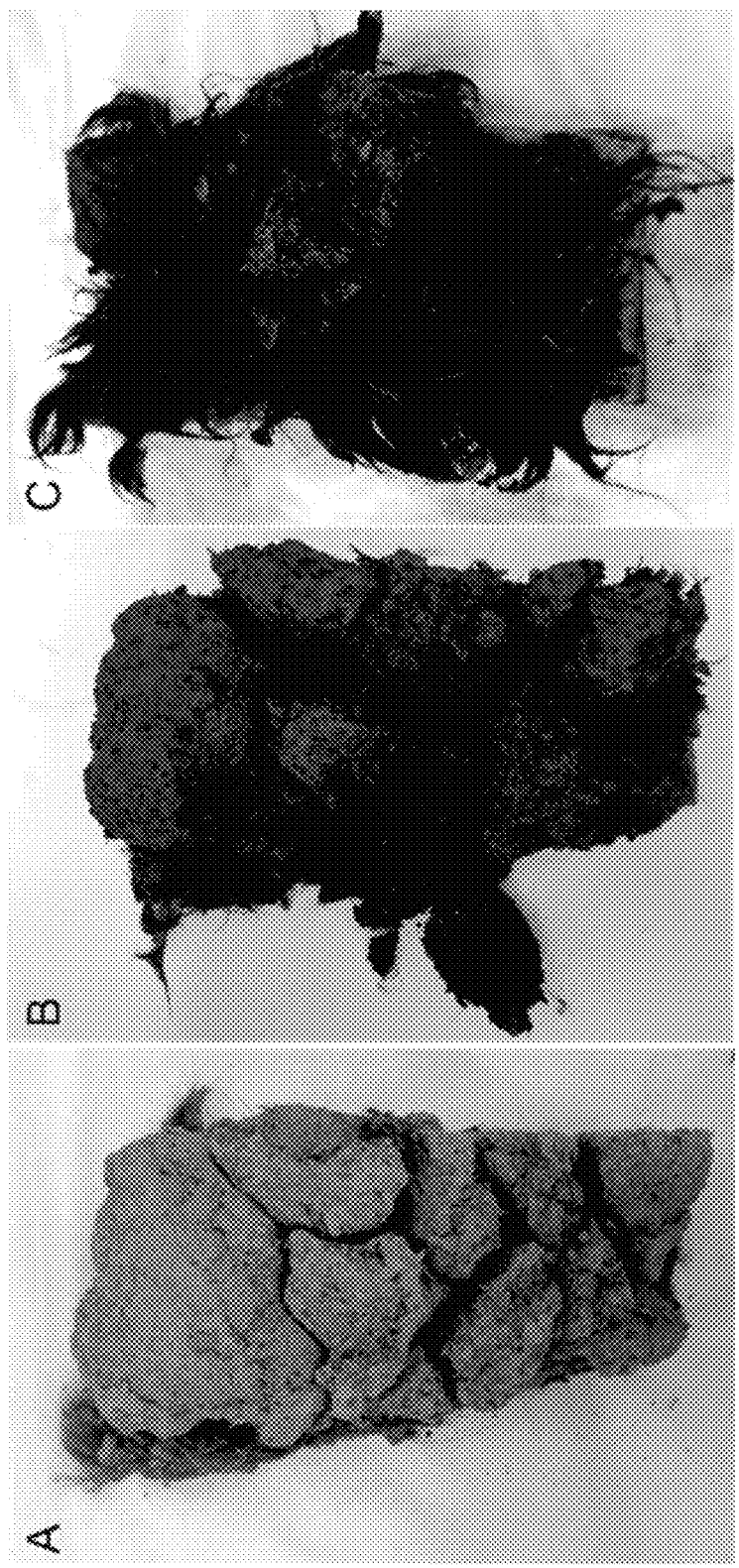
FIGS. 15A-15C: Hide treated with 10 U/mL Ronozyme ProAct in 2% sodium thioglycolate and 5% Triton X-100. Hide before treatment (FIG. 15A), after 16 hours treatment at room temperature (FIG. 15B), after 3 minutes mid pressure water washing (FIG. 15C).

A small piece of hide (15×9 cm) with dags attached was treated with 10 U/mL Ronozyme ProAct in the presence of 2% sodium thioglycolate and 5% Triton X-100 (FIG. 8). After 16 hours treatment at room temperature, dags appeared loosely attached to the hide after 16 hours of treatment at room temperature and easily came off with 3 minutes of mid pressure water washing at the sink (FIG. 15C).

Discussion

In this work we studied the effect on dag decomposition using commercial enzymes for biomass degradation from several companies (DSM, Dupont and Novozymes). Each of these enzymes was assayed for specific activity and applied in different combinations and concentration to dag samples. Decomposition was assessed with spatula testing and quantified by measurement of enzyme derived products in solution after treatment.

Individual treatment of dag with biomass degrading enzymes (α-amylase, cellulase and xylanase) had some effect on decomposition, however, the degree of breakdown was enhanced when these enzymes where applied in combination. From the spatula testing however we felt that the extent of degradation obtained was not sufficient for the reliable removal of dags from cattle. Higher concentrations of enzymes might be needed to archive this goal but the experiments showed that a five-fold increase, whilst increasing the amount of soluble sugars, did not increase dag degradation and would add additional costs. The addition of surfactants to the enzymatic formulation appeared to facilitate the permeabilisation of the dag structure enhancing enzymatic degradation. According to our studies, Triton X-100 and Saponin showed best results when compared to other surfactants. Saponin is a food grade surfactant that could be easily incorporated in an enzymatic formulation for animal application.

We also pursued an alternative approach for dag decomposition that consisted of attacking the interaction between the hair and the dag as well as any residual feed protein that may act like a glue in the dag. For this, we tested Ronozyme ProAct, a commercial protease from DSM-Novozymes, previously shown in our lab to be very effective towards keratin breakdown (ref keratinase paper). We also included sodium sulfite or sodium thioglycolate as reducing agents to the treatment of dag with keratinase. According to our previous work, hair samples treated with keratinase and these reducing agents were extensively degraded (ref keratinase paper). When we applied a mixture of keratinase, reducing agent and surfactant to dag samples we found significant dag breakdown. Similar dag decomposition results were observed when sodium sulfite or sodium thioglycolate where added to the treatment; nevertheless, enhanced results were observed with sodium thioglycolate during hair treatments at low temperature (22° C.). In addition, sodium sulfite is a food grade compound and its inclusion in the formulation for animal applications might be straightforward from a regulatory perspective. It should be noted that Ronozyme ProAct is approved for use with livestock, as are most of the enzymes tested during this work.

The results of this study suggest a possible hypothesis for dag formation and degradation. According to this hypothesis, the dag biomass (mainly lignocellulosic material) accumulates on a patch of hair fibres. The mixture of dung, soil, urine, straw and partially digested grains initially deposits on hide hairs and continues to build on layer after layer until the clump like aggregate is formed. The long hair fibres within the dag are the scaffold that support the structure with the lignocellulose components held together by constituents in the dag that can act like a glue (i.e. sugars, starch and protein would all act in this way once dried). Given that amylase for starch degradation was relatively ineffective compared to protease/keratinase we hypothesise that the presence of feed protein contributes to the generation of the glue-like component that helps the layers of biomass adhere into a compact, recalcitrant dag aggregate. MLA project FLOT.214 detected 13-17% of protein component in Australian dags (Slattery et al. 2005). Attacking the hair fibre scaffold, the point of attachment between the hair and the dag and the adhesive protein component using keratinases and reducing agents breaks down the dag framework structure and facilitates decomposition. The addition of surfactants aids the permeation of the treatment solution and accessibility of the keratinase to internal hairs. The combination of keratinase and biomass degrading enzymes did not seem to further improve dag breakdown. Since the majority of the lignocellulose particles present in dags have been through animal digestion, we believe they are already too small to provide structural strength and degrading them even further with biomass degrading enzymes does not have a noticeable effect. The key strategy is therefore to attack the structural framework and the binding agent, which we propose are the hairs and the feed protein component respectively.

Conclusion

In this work, we studied biomass degrading enzymes and a keratinase for dag decomposition from Australian cattle hides. The treatment with enzymes targeting lignocellulosic material and starch had an effect on dag deconstruction, that was enhanced when the enzymes (cellulase, α-amylase and xylanase) where added in combination, however, variable results were observed. The treatment with keratinase showed extensive degree of breakdown of dag samples that was not further improved with a two-step treatment using keratinase and biomass degrading enzymes. As a result of this work, we propose an enzymatic system for the decomposition of dags that involves a keratinase enzyme (Ronozyme ProAct), a reducing agent and a surfactant. According to our results, 2% sodium thioglycolate or 1% sodium sulfite can be incorporated as reducing agent and 5% Triton X-100 or Saponin as surfactant to a future formulation. Assessment of the proposed dag cleaning formulation on hide samples from more geographic areas with different feeding regimes to more fully assess the effect of dag variability (e.g. to assess changes in composition, protein type (e.g. grain or sorghum) hardness and size) should be conducted in future studies. This work provides a solution to the problem of dag removal in Australia, which could be extended to different parts of the world, improving animal welfare and reducing significant costs to the industry.

Throughout the specification the aim has been to describe the preferred embodiments of the invention without limiting the invention to any one embodiment or specific collection of features. It will therefore be appreciated by those of skill in the art that, in light of the instant disclosure, various modifications and changes can be made in the particular embodiments exemplified without departing from the scope of the present invention.

All scientific and patent literature referred to herein are incorporated by reference in their entirety.

REFERENCES

Bradford, M. M. (1976). "A rapid and sensitive method for the quantitation of microgram quantities of protein utilizing the principle of protein-dye binding." *Analytical biochemistry* 72(1-2): 248-254.

Brandelli, A., D. J. Daroit and A. Riffel (2010). "Biochemical features of microbial keratinases and their production and applications." *Applied Microbiology and Biotechnology* 85(6): 1735-1750.

Caldas, C., A. Cherqui, A. Pereira and N. Simoes (2002). "Purification and characterization of an extracellular protease from Xenorhabdus nematophila involved in insect immunosuppression." *Applied and environmental microbiology* 68(3): 1297-1304.

Cassells, J. and V. Haritos (2009). MLA Final Report B.FLT.0226.

Cavello, I., S. Cavalitto and R. Hours (2012). "Biodegradation of a keratin waste and the concomitant production of detergent stable serine proteases from Paecilomyces lilacinus." *Applied biochemistry and biotechnology* 167 (5): 945-958.

Covington, A., C. Evans and M. Tozan (1999). Enzymatic removal of dung from hides and skins. Proceedings of the XXV IULTCS Congress: 355-362.

Covington, A. D. and C. S. Evans (2003). Cleaning animal skins

Daroit, D. J. and A. Brandelli (2014). "A current assessment on the production of bacterial keratinases." *Critical reviews in biotechnology* 34(4): 372-384.

FSA. (2007). "Clean Beef Cattle for slaughter. A guide for producers." from www.foodstandards.gov.uk/publications.

Gegeckas, A., R. Gudiukaite, J. Debski and D. Citavicius (2015). "Keratinous waste decomposition and peptide production by keratinase from Geobacillus stearothermophilus AD-1." *International journal of biological macromolecules* 75: 158-165.

Huang, Q., Y. Peng, X. Li, H. Wang and Y. Zhang (2003). "Purification and characterization of an extracellular alkaline serine protease with dehairing function from Bacillus pumilus." Current microbiology 46(3): 0169-0173.

Huang, Y., P. K. Busk, F.-A. Herbst and L. Lange (2015). "Genome and secretome analyses provide insights into keratin decomposition by novel proteases from the non-pathogenic fungus *Onygena corvina.*" *Applied microbiology and biotechnology* 99(22): 9635-9649.

Jaouadi, N. Z., H. Rekik, A. Badis, S. Trabelsi, M. Belhoul, A. B. Yahiaoui, H. B. Aicha, A. Toumi, S. Bejar and B. Jaouadi (2013). "Biochemical and molecular characterization of a serine keratinase from *Brevibacillus brevis* US575 with promising keratin-biodegradation and hide-dehairing activities." *PloS one* 8(10): e76722.

Jeong, J.-H., O.-M. Lee, Y.-D. Jeon, J.-D. Kim, N.-R. Lee, C.-Y. Lee and H.-J. Son (2010). "Production of keratinolytic enzyme by a newly isolated feather-degrading *Stenotrophomonas maltophilia* that produces plant growth-promoting activity." *Process biochemistry* 45(10): 1738-1745.

Khandelwal, H. B., S. V. More, K. Kalal and R. S. Laxman (2015). "Eco-friendly enzymatic dehairing of skins and hides by *C. brefeldianus* protease." *Clean Technologies and Environmental Policy* 17(2): 393-405.

Kuhad, R. C., R. Gupta and A. Singh (2011). "Microbial cellulases and their industrial applications." *Enzyme research* 2011.

Lange, L., Y. Huang and P. K. Busk (2016). "Microbial decomposition of keratin in nature—a new hypothesis of industrial relevance." *Applied microbiology and biotechnology* 100(5): 2083-2096.

Lin, X., C.-G. Lee, E. S. Casale and J. C. Shih (1992). "Purification and characterization of a keratinase from a feather-degrading *Bacillus licheniformis* strain." *Applied and Environmental Microbiology* 58(10): 3271-3275.

McKittrick, J., P.-Y. Chen, S. Bodde, W. Yang, E. Novitskaya and M. Meyers (2012). "The structure, functions, and mechanical properties of keratin." *Jom* 64(4): 449-468.

Miller, G. L. (1959). "Use of dinitrosalicylic acid reagent for determination of reducing sugar." *Analytical chemistry* 31(3): 426-428.

Pauly, M. and K. Keegstra (2008). "Cell-wall carbohydrates and their modification as a resource for biofuels." *The Plant Journal* 54(4): 559-568.

Riffel, A., A. Brandelli, C. d. M. Bellato, G. H. Souza, M. N. Eberlin and F. C. Tavares (2007). "Purification and characterization of a keratinolytic metalloprotease from *Chryseobacterium* sp. kr6." *Journal of Biotechnology* 128(3): 693-703.

Slattery, B., J. Davis and B. Carmody (2005). "MLA Final Report FLOT.214."

Vijayaraghavan, P., S. Lazarus and S. G. P. Vincent (2014). "De-hairing protease production by an isolated *Bacillus cereus* strain AT under solid-state fermentation using cow dung: Biosynthesis and properties." *Saudi journal of biological sciences* 21(1): 27-34.

The invention claimed is:

1. A method of removing, at least in part, a biological deposit from skin of an animal, wherein the biological deposit is or comprises animal faeces, including the step of administering to the biological deposit an effective amount of a composition comprising:
 a protease having keratinolytic activity; and
 a reducing agent;
 to thereby remove the biological deposit from the animal.

2. The method of claim 1, wherein the reducing agent is or comprises a sulfur containing compound.

3. The method of claim 2, wherein the reducing agent is selected from the group consisting of a sulphite, a thiol, a cysteine and any combination thereof.

4. The method of claim 1, wherein the composition further comprises a surfactant.

5. The method of claim 4, wherein the surfactant is or comprises a non-ionic surfactant and/or a wetting agent.

6. The method of claim 4, wherein the surfactant is selected from the group consisting of an alkylphenol ethoxylate, a saponin, an isotridecanol polyglycol ether, a polyoxyethylene alkyl ether, and any combination thereof.

7. The method of claim 6, wherein the polyoxyethylene alkyl ether is or comprises a polyoxyethylene octyl phenyl ether, a polyoxyethylene (20) cetyl ether or any combination thereof.

8. The method of claim 1, further including the step of washing the biological deposit.

9. A composition for removing, at least in part, a biological deposit from skin of an animal, wherein the biological deposit is or comprises animal faeces, the composition comprising:
 a protease having keratinolytic activity;
 a reducing agent comprising a thioglycolate salt; and
 a surfactant.

10. The composition of claim 9, wherein the surfactant is or comprises a non-ionic surfactant and/or a wetting agent.

11. The composition of claim 9, wherein the surfactant is selected from the group consisting of an alkylphenol ethoxylate, a saponin, an isotridecanol polyglycol ether, a polyoxyethylene alkyl ether, and any combination thereof.

12. The composition of claim 11, wherein the polyoxyethylene alkyl ether is or comprises a polyoxyethylene octyl phenyl ether, a polyoxyethylene (20) cetyl ether or any combination thereof.

13. A method of preparing a composition for removing, at least in part, a biological deposit from a portion of skin of an animal, wherein the biological deposit is or comprises animal faeces, said method including the step of mixing a protease having keratinolytic activity, a reducing agent comprising a thioglycolate salt, and a surfactant, to thereby prepare the composition.

14. The method of claim 1, wherein the animal is bovine.

15. The composition of claim 9, wherein the animal is bovine.

16. The method of claim 1, wherein the animal is a live animal.

* * * * *